US007655241B2

(12) United States Patent
Klimpel et al.

(10) Patent No.: US 7,655,241 B2
(45) Date of Patent: Feb. 2, 2010

(54) METHODS AND COMPOSITIONS FOR VACCINATION AGAINST OR INVOLVING ENTEROBACTERIACEAE BACTERIA

(75) Inventors: Gary R. Klimpel, Santa Fe, TX (US); David W. Niesel, Friendswood, TX (US); Ashok Chopra, League City, TX (US); Jian Sha, League City, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 115 days.

(21) Appl. No.: 10/394,517

(22) Filed: Mar. 20, 2003

(65) Prior Publication Data

US 2003/0215464 A1 Nov. 20, 2003

Related U.S. Application Data

(60) Provisional application No. 60/366,346, filed on Mar. 21, 2002.

(51) Int. Cl.
| | |
|---|---|
| A61K 39/02 | (2006.01) |
| A61K 48/00 | (2006.01) |
| A61K 39/112 | (2006.01) |
| A61K 39/38 | (2006.01) |
| A01N 63/04 | (2006.01) |
| C12N 15/09 | (2006.01) |
| C12P 21/06 | (2006.01) |
| C12P 21/04 | (2006.01) |

(52) U.S. Cl. ............... 424/200.1; 424/93.48; 424/93.2; 424/258.1; 424/234.1; 424/184.1; 435/69.3; 435/69.1; 435/69.7

(58) Field of Classification Search .............. 424/93.48, 424/93.4, 93.2, 200.1, 241.1, 258.1, 234.1; 435/71.1, 71.2, 69.3, 69.1, 69.7, 59.7
See application file for complete search history.

(56) References Cited

U.S. PATENT DOCUMENTS

| 4,624,926 | A | * | 11/1986 | Inouye et al. | .......... 435/252.33 |
|---|---|---|---|---|---|
| 5,348,867 | A | * | 9/1994 | Georgiou et al. | ........... 435/69.7 |
| 5,554,372 | A | * | 9/1996 | Hunter | .................... 424/280.1 |
| 6,605,709 | B1 | * | 8/2003 | Breton | ...................... 536/23.1 |
| 6,610,836 | B1 | * | 8/2003 | Breton et al. | .............. 536/23.1 |
| 2003/0131376 | A1 | * | 7/2003 | Okubara et al. | ............. 800/278 |

FOREIGN PATENT DOCUMENTS

EP 0300459 * 1/1989

OTHER PUBLICATIONS

Zwiebel et al. J. Bacteriol. 145: 654-656, 1981.*
Gupta et al. J. Biol. Chem. 268: 16551-16556, 1993.*
Nakamura et al. EMBO J. 1: 771-775, 1982.*
Zhang et al. J. Immunol. 159: 4868-4878, 1997.*
Zhang et al. Infect. Immun. 66: 5196-5201, 1998.*
Kanamori et al. Gene 66: 295-300, 1988.*
Beck et al. J. Bacteriol. 181: 7285-7290, 1999.*
Sambrook et al. Molecular Cloning. A Laboratory Manual. Second Edition, Cold Spring Harbor, pp. 17.1-17.44, 1989.*
Henriksen et al. APMIS 97: 559-568, 1989.*
Nakamura et al. PNAS 77: 1369-1373, 1980.*
Brett et al., *J. Immunol.*, "Comparison of antigen presentation of influenza a nucleoprotein expressed in attenuated aroA- *Salmonella typhimurium* with that of live virus,"150:2869-2884, 1993.
Ching and Inouye, "Evolution of the lipoprotein gene in the enterobacteriaceae—cloning and DNA sequence of the Ipp gene from *Proteus mirabilis*," *J. Mol. Biol.*, 185:501-507, 1985.
Coynault et al., *Mol. Microbiol.*, "Virulence and vaccine potential of *Salmonella typhimurium* mutants deficient in the expression of the RpoS ([sigma]s) regulon," 22:149-160, 1996.
Fouts et al., "Construction and immunogenicity of *Salmonella typhimurium* vaccine vector that express HIV-1 gp120," *Vaccine*, 13:1697-1705, 1995.
Huang et al., "Comparison of the lipoprotein gene among the enterobacteriaceae," *J. Biol. Chem.*, 258:8139-8145, 1983.
Nakamura and Inouye, "DNA Sequence of the gene for the outer membrane lipoprotein of *E. coli*: an extremely AT-rich promoter," *Cell*, 18:1109-1117, 1979.
Noriega et al., "Engineered ΔaguaB-A ΔvirG Shigella flexneri 2a strain CVD 1205: construction, safety, immunogenicity, and potential effecacy as a mucosal vaccine," *Infect. Immun.*, 64:3055-3061, 1996.
Sizemore et al, "Attenuated Shigella as a DNA delivery vehicle for DNA-mediated immunization," *Science*, 270:299-302, 1995.
Yamagata et al., "Comparison of the lipoprotein gene among the enterobacteriaceae,"*J. Biol. Chem.*, 256:2194-2198, 1981.

* cited by examiner

*Primary Examiner*—S. Devi
(74) *Attorney, Agent, or Firm*—Fulbright & Jaworski L.L.P.

(57) ABSTRACT

The present invention concerns the use of methods and compositions to prophylactically or therapeutically vaccinate a subject against a pathogen or disease. Embodiments of the invention include the production of an attenuated bacterium from the family Enterobacteriaceae with a non-functional lipoprotein for use as a vaccine or as a vaccine vector for delivering antigens to a subject to be vaccinated. In certain embodiments, a bacterium of the Enterobacteriaceae family lacking a wild type LP, for example *Salmonella typhimurium* lacking a wild type LP, may be produced and used as a vaccine or vaccine vector.

26 Claims, 9 Drawing Sheets

Table 1. DNA Sequence Homology Between the *lp* genes of *Salmonella typhimurium* and *E. coli*

| Organism | % Homology |
|---|---|
| *E. coli lp*<br>*S. typhimurium lp* 1 | 96.2% |
| *E. coli lp*<br>*S. typhimurium lp* 2 | 78.8% |
| *S. typhimurium lp* 1<br>*S. typhimurium lp* 2 | 79.2% |

FIG. 8

Table 2. Amino Acid Sequence Homology Between LP of *E. coli* and *S. typhimurium*

```
                                  15                     30                      45
E. coli LP         MKAT-KLVLGAVILG STLLAGCSSNAKIDQ LSSDVQTLNAKVDQL
S. typhimurium LP 1 MNRT-KLVLGAVILG STLLAGCSSNAKIDQ LSSDVQTLNAKVDQL
S. typhimurium LP 2 MNRTNQLILGAVVLG STLLAGCSSNAKIDQ LSSDVQTLSAKVEQL 60                      75   79
E. coli LP         SNDVNAMRSDVQAAK DDAARANQRLDNMAT KYRK
S. typhimurium LP 1 SNDVNAMRSDVQAAK DDAARANQRLDNQAT KYRK
S. typhimurium LP 2 SNDVNAMRSDVQAAK DDAARANQRLDNKVF RICK
```

| Organism | % Homology |
|---|---|
| *E. coli* LP<br>*S. typhimurium* LP 1 | 97% |
| *E. coli* LP<br>*S. typhimurium* LP 2 | 84% |
| *S. typhimurium* LP 1<br>*S. typhimurium* LP 2 | 86% |

FIG. 9

METHODS AND COMPOSITIONS FOR VACCINATION AGAINST OR INVOLVING ENTEROBACTERIACEAE BACTERIA

This application claims priority to U.S. Provisional Patent application Ser. No. 60/366,346 filed on Mar. 21, 2002, which is incorporated herein by reference in its entirety.

BACKGROUND OF THE INVENTION

1. Field of the Invention

The present invention relates generally to the fields of microbiology and immunology. More particularly, it concerns methods and compositions for vaccination against bacteria in the family Enterobacteriaceae, as well as methods and compositions for vaccination against any heterologous peptide or polypeptide expressed by a bacterium in the family Enterobacteriaceae.

2. Description of Related Art

Vaccines are a medical tool for the prophylactic and therapeutic treatment of infectious diseases, including infectious diseases caused by bacteria, viruses, parasites, fungi and other pathogens. In addition to affording protection against infectious diseases, vaccines may now also be developed to stimulate the host's immune system to recognize cells with aberrant growth characteristics, such as tumor cells.

Host immune responses include both the humoral immune response involving antibody production and the cell-mediated immune response. Protective immunization via vaccine has usually been designed to induce the formation of humoral antibodies directed against infectious agents, tumor cells, or toxins. The control of certain diseases characterized by the presence of tumor cells or by chronic infection of cells with infectious agents, often requires a cell-mediated immune response either in place of, or in addition to the generation of antibody. While the humoral immune response may be induced using live infectious agents and agents which have been inactivated, a cellular immune response is most effectively induced through the use of live agents as vaccines. Such live agents include live infectious agents which may gain access to the host cells where the proteins encoded by these agents are processed into epitopes, which when presented to the cellular immune system, induce a protective response.

Microorganisms, such as *Salmonella* and *Shigella*, which have been attenuated using a variety of mechanisms, have been examined for their ability to encode and express heterologous antigens (Coynault et al., 1996; Noriega et al., 1996; Brett et al., 1993, Fouts et al., 1995; and Sizemore et al., 1995). Such bacteria may be useful as live attenuated bacterial vaccines, which serve to induce a cellular immune response directed against a desired heterologous antigen.

Although the potential broad use of attenuated bacteria as a vaccine or vaccine vector for the prevention and treatment of infectious disease and cancer has significant advantages over other vaccines, the issue of safety during use of attenuated bacteria are not trivial. The use of an attenuated strain of *Listeria monocytogenes* is accompanied by potentially severe side effects, including the development of listeriosis in the inoculated animal. One group of individuals that might benefit from the use of an attenuated bacteria as a vaccine or vaccine vector are individuals who are infected with HIV. However, because these individuals are severely immunocompromised as a result of their infection, the use of attenuated bacteria as a vaccine or vaccine vector is undesirable unless the bacteria are fully and irreversibly attenuated.

There is a need for the development of bacterial strains for use as vaccines and vaccine vectors that are attenuated to the extent that they are unable to cause disease in an individual into whom it is inoculated, but still able to develop cell mediated immune responses.

SUMMARY OF THE INVENTION

The present invention is based on the creation of a Enterobacteriaceae bacterium lacking a functional lipoprotein (LP) and on the observation that such a bacterium's virulence is attenuated, yet is capable of inducing an immune response. Thus, the present invention concerns compositions and methods for producing bacterium lacking a functional lipoprotein, which may or may not harbor a heterologous nucleic acid sequence, and generating an immune response against the bacterium and/or the heterologous sequence.

The present invention is directed to any gram-negative bacteria that express lipoprotein (LP) or has an lpp gene (also known as llp gene). In some embodiments of the invention, bacteria of the invention are of the Enterobacteriaceae family. Bacteria of the invention do not express a wild-type lipoprotein, and in some embodiments, do not express a functional lipoprotein. The term "lipoprotein deficient" may be used to describe a bacterium that is not able to express a functional lipoprotein on the surface of the bacterium. The bacterium may be lipoprotein deficient due to the inability to transcribe, translate, transport, localize or function as a non-modified lipoprotein would. The term "functional lipoprotein" refers to a lipoprotein that confers the same degree of infectivity as wild-type lipoprotein in a host. Thus, a bacterium with a functional lipoprotein and a comparable genotype as a second bacterium, except that the second bacterium expresses wild-type lipoprotein, will have the same degree of infectivity (i.e., infectivity within a standard deviation of one another) depending on the assay used for infectivity. The infectivity of a bacterium lacking a functional lipoprotein will be attenuated, reduced, lessened, or eliminated as compared to a bacterium having a functional lipoprotein. In some embodiments, a bacterium does not have a functional lipoprotein because it lacks any lipoprotein. A bacterium may lack lipoprotein because it lacks at least all or part of one lpp gene. In some embodiments, the bacterium lacks all or part of more than one lpp gene, such as both or all of them. In some embodiments of the invention, the bacterium lacks all of at least one lpp gene, while in other embodiments, the bacterium lacks all of at least two or all lpp genes.

At least one lpp gene of bacteria of the invention may be mutated. An lpp gene may be mutated so it does not or cannot express a lipoprotein. In some cases, an lpp gene has a deletion, substitution, or insertion mutation. Mutations may be created by randomly or by specifically mutating a wild-type LP-encoding sequence or by identifying such a naturally occurring mutation. The mutations may introduce a frameshift and/or introduce a premature stop codon. In still further embodiments, the mutation is a point mutation. Alternatively, a mutation may involve more than one nucleotide. In some embodiments, the mutation involves 1, 2, 3, 4, 5, 6, 7, 8, 9, 10, 15, 20, 30, 40, 50, 60, 70, 80, 90, 100, 110, 120, 130, 140, 150, 160, 170, 180, 190, 200, 250, 300, 350, 400, 450, 500, 550, 600, 650, 700, 750, 800, 850, 900, 950, 1000 or more nucleotides, or at least or at most that many nucleotides of an lpp gene (e.g., SEQ ID NO: 1, 3, or 5). It is further contemplated that a mutation results in a change affecting 1, 2, 3, 4, 5, 6, 7, 8, 9, 10, 15, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 or more amino acids of a wild type lipoprotein polypeptide (e.g., SEQ ID NO: 2, 4, 6, 7, or 8).

In some embodiments of the invention, the mutation is a substitution that leads to a nonhomologous change, for example, when a charged residue is substituted for an uncharged residue, or vice versa. In other embodiments, the mutation is a deletion that results in a truncated lipoprotein. In some embodiments, an lpp gene is modified to encode a fusion protein comprising all or part of a lipoprotein and a heterologous peptide or polypeptide. In specific embodiments, the lpp gene expresses a fusion protein comprising a truncated lipoprotein.

Compositions of the invention also concern bacteria of the family Enterobacteriaceae that comprise a heterologous nucleic acid sequence, in addition to lacking a functional lipoprotein. The term "heterologous" with respect to a nucleic acid or nucleic acid sequence refers to a nucleic acid or sequence that does not naturally occur in a particular context, such as the genome or in the cell of a particular organism, and likely occurs in embodiments of the invention as a result of recombinant DNA manipulations or techniques. Thus, for example, if a bacterium from the family Enterobacteriaceae contains a nucleic acid sequence not found in any bacteria of the Enterobacteriaceae family, the sequence is heterologous to bacteria in the Enterobacteriaceae family. Furthermore, the term "heterologous" with respect to an amino acid or amino acid sequence refers to an amino acid or sequence that does not naturally occur in a particular organism, such as a bacterium of the Enterobacteriaceae family. Thus, in some embodiments, the present invention concerns bacteria of the Enterobacteriaceae family that contain heterologous nucleic acid sequences and/or express heterologous amino acids sequences, i.e, non-Enterobacteriaceae sequences. Such bacteria may be used as a vaccine or vaccine vector. A vaccine refers to a preparation of a weakened or killed pathogen, or of a portion of the pathogen's structure that stimulates an immune response against the pathogen but is incapable of causing a severe infection. A vaccine vector refers to a composition that delivers, localizes, or presents a heterologous antigen, epitope, or immunogen to a subject in a manner that stimulates, elicits, or induces an immune response. The vaccine vector itself, excluding any heterologous antigen that may be associated with the vaccine vector, may or may not be antigenic.

As the present invention concerns vaccines, a heterologous nucleic acid sequence in a bacterium of the Enterobacteriaceae family includes any sequence encoding an antigen or immunogen against which an immune response is desired. The heterologous nucleic acid sequence may be chromosomally integrated in the genome of the bacterium or it may be carried episomally. In embodiments in which the sequence is chromosomally integrated, the sequence may be inserted into an lpp gene or the sequence may replace all or part of an lpp gene(s). In some embodiments of the invention, a bacterium comprises an expression cassette comprising a nucleic acid encoding an antigen. The antigen may be heterologous with respect to the organism in which the immune response will be generated. In some embodiments, the antigen is obtained or derived from a pathogenic organism. In still further embodiments, the pathogenic organism is a bacterium, a fungus, a virus, a nematode, a trypanosome, or an amoebae.

In some embodiments, the antigen is or constitutes part of a fusion protein. The fusion protein may include a pro, prepro, or similar sequence that localize or direct the movement or localizes a fusion protein to the cell surface. A signal sequence or signal peptide may be a short sequence that directs newly synthesized protein to or through a membrane. A signal sequence is typically, but not universally positioned at the N-terminus of a protein and may be cleaved by a signal peptidase. In other embodiments, the cell may express an antigen within the cell and upon biologic processing of the cell by the bodies immune system the antigen is presented, thus, not requiring a signal sequence. Other embodiments may secrete the antigen by fusion of the antigen to a secretory sequence. See Von Heijne, 1985, incorporated herein by reference, for a review of signal sequences. In certain embodiments, a fusion protein may comprise an antigen sequence fused to the signal sequence of the LP protein. The fusion protein may be expressed on the surface of the bacterium.

An Enterobacteriaceae bacterium of the invention expressing a heterologous amino acid sequence as a vaccine against the heterologous amino acid sequence constitutes a vaccine vector, which is part of the present invention. Vaccine vectors may comprise any of the bacteria discussed herein.

Enterobacteriaceae bacteria of the invention may be any bacteria from that family, and specifically includes, but is not limited to, bacteria of the following genera: *Escherichia coli, Shigella, Edwardsiella, Salmonella, Citrobacter, Klebsiella, Enterobacter, Serratia, Proteus, Erwinia, Morganella, Providencia,* or *Yersinia*. In more specific embodiments, the bacterium is of the *E. coli, E. blattae, E. fergusonii, E. hermanii, E. vuneris, Salmonella enterica, Salmonella typhimurium, Salmonella salamae, Salmonella arizonae, Salmonella diarizonae, Salmonella houtenae, Salmonella bongori, Salmonella indica, Shigella dysenteriae, Shigella flexneri, Shigella boydii, Shigella sonnei, Enterobacter aerogenes, Enterobacter gergoviae, Enterobacter sakazaki, Enterobacter cloacae, Enterobacter agglomerans, Klebsiella pneumoniae, Serratia marcescens, Yersinia pseudotuberculosis, Yersinia pestis, Yersinia enterocolitica, Erwinia, Proteus mirabilis, Proteus vulgaris, Proteus penneri, Proteus hauseri, Providencia alcalifaciens,* or *Morganella morganii* species.

Bacteria, vaccine vectors, and vaccines of the invention may be in a pharmaceutically acceptable composition. Such compositions may further comprise an adjuvant. In some embodiments, the adjuvant is Adjumer™, Adju-Phos, Algal Glucan, Algammulin, Alhydrogel, Antigen Formulation, Avridine®, BAY R1005, Calcitriol, Calcium Phosphate Gel, Cholera holotoxin (CT), Cholera toxin B subunit (CTB), Cholera toxin A1-subunit-Protein A D-fragment fusion protein, CRL1005, Cytokine-containing Liposome, Dimethyl dioctadecylammonium bromide, Dehydroepiandrosterone; Dimyristoyl phosphatidylcholine; 1,2-dimyristoyl-sn-3-phosphatidylcholine, Dimyristoyl phosphatidylglycerol, Deoxycholic Acid Sodium Salt; Freund's Complete Adjuvant, Freund's Incomplete Adjuvant, Gamma Inulin, Gerbu Adjuvant, GM-CSF, N-acetylglucosaminyl-($\beta$1-4)-N-acetylmuramyl-L-alanyl-D-isoglutamine, Imiquimod, ImmTher™, Interferon-$\gamma$, Interleukin-1$\beta$, Interleukin-2, Interleukin-7, Interleukin-12, ISCOM™, Iscoprep 7.0.3.™, Liposome, Loxoribine, LT-OA or LT Oral Adjuvant, MF59, MONTANIDE ISA 51, MONTANIDE ISA 720, MPL™, MTP-PE, MTP-PE Liposome, Murametide, Murapalmitine, D-Murapalmitine, NAGO, Non-Ionic Surfactant Vesicle, Pleuran, lactic acid polymer, glycolic acid polymer, Pluronic L121, Polymethyl methacrylate, PODDS™, Poly rA:Poly rU, Polysorbate 80, Protein Cochleate, QS-21, Quil-A, Rehydragel HPA, Rehydragel LV, S-28463, SAF-1, Sclavo peptide, Sendai Proteoliposome, Sendai-containing Lipid Matrix, Span 85, Specol, Squalane, Squalene, Stearyl Tyrosine, Theramide™, Threonyl-MDP, Ty Particle, or Walter Reed Liposome.

Methods of the invention involve using bacteria, vaccines, and vaccine vectors of the invention to induce an immune response. The immune response may be against the bacteria and/or it may be against a heterologous nucleic acid or amino acid sequence in a bacterium. In some embodiments of the invention, methods for inducing an immune response in a subject against a bacterium of the family Enterobacteriaceae comprise administering to the subject an effective amount of a composition comprising a bacterium of the family Enterobacteriaceae, wherein an immune response is induced against the bacterium. Methods of the invention may involve any of the compositions discussed herein, including the various embodiments involving bacteria.

In some embodiments of the invention, a subject is a mammal, including a human. It is contemplated that the subject may be administered vaccine, vaccine vector, and bacterial compositions of the invention at least two times. Compositions may be administered 2, 3, 4, 5, 6, 7, 8, 9, 10 or more times, and furthermore, they may be administered hourly, daily, weekly, biweekly, monthly, bimonthly or annually. In some methods of the invention, a subject is administered about $10^3$ to about $10^{11}$ colony forming unite (cfu) or about $10^3$ to about $10^{15}$ cfu, though the subject may be administered about or at least about $10^3$, $10^4$, $10^5$, $10^6$, $10^7$, $10^8$, $10^9$, $10^{10}$, $10^{11}$, $10^{12}$, $10^{13}$, $10^{14}$, or $10^{15}$ cfu. A dosage may be determined empirically and depends to some extent on the characteristics of the attenuated bacterium. Compositions may be administered intravenously, intramuscularly, subcutaneously, orally, or intraperitoneally.

Methods of the invention further include vaccinating a subject against a bacterium of the family Enterobacteriaceae comprising administering to the subject the bacterium in a pharmaceutically acceptable composition, wherein the bacterium lacks a wild type lipoprotein. Other embodiments of the invention include vaccinating a subject against any pathogen comprising administering to the subject a composition comprising a bacterium comprising a heterologous nucleic acid sequence encoding an antigen from the pathogen, wherein the bacterium lacks a wild type or functional lipoprotein. In specific embodiments, a methods of the invention include vaccinating a subject against *Salmonella tymphimurium* comprising administering to the subject a *Salmonella typhimurium* in a pharmaceutically acceptable composition, wherein the *Salmonella typhimurium* lacks a wild type lipoprotein. As previously stated, any composition discussed herein may be employed in any methods of the invention. Methods may be directed at immunizing or vaccinating against any composition of the invention. including any antigen. Thus, in some embodiments of the invention, methods for inducing an immune response against an antigen in a subject is contemplated. In such methods, a subject is administered an effective amount of a lipoprotein-deficient bacterium of the Enterobacteriaceae family, wherein bacterium comprises an expression cassette encoding the antigen. As discussed above, antigens may include, but are not limited to, viral, bacterial, fungal, or other pathogenic antigens.

The invention also includes methods for producing a vaccine for a bacterial infection comprising generating a bacterium of the family Enterobacteriaceae lacking functional lipoprotein and formulating a pharmaceutically acceptable composition comprising the bacterium. In some embodiments, the bacterium is a progeny bacterium from a bacterium recombinantly manipulated to lack a functional lipoprotein. A progeny bacterium refers to any successive generation of bacterium.

It is contemplated that any embodiment discussed with respect to one aspect of the invention may be implemented or employed with respect to any other aspect of the invention.

The use of the word "a" or "an" when used in conjunction with the term "comprising" in the claims and/or the specification may mean "one," but it is also consistent with the meaning of "one or more," "at least one," and "one or more than one."

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 8 illustrates the DNA sequence homology between lpp genes of *Salmonella typhimurium* and *E. coli*.

FIG. 9 illustrates the amino acid sequence homology between LP of *Salmonella typhimurium* and *E. coli* (SEQ ID NOS:6-8).

DESCRIPTION OF ILLUSTRATIVE EMBODIMENTS

Figure 1:
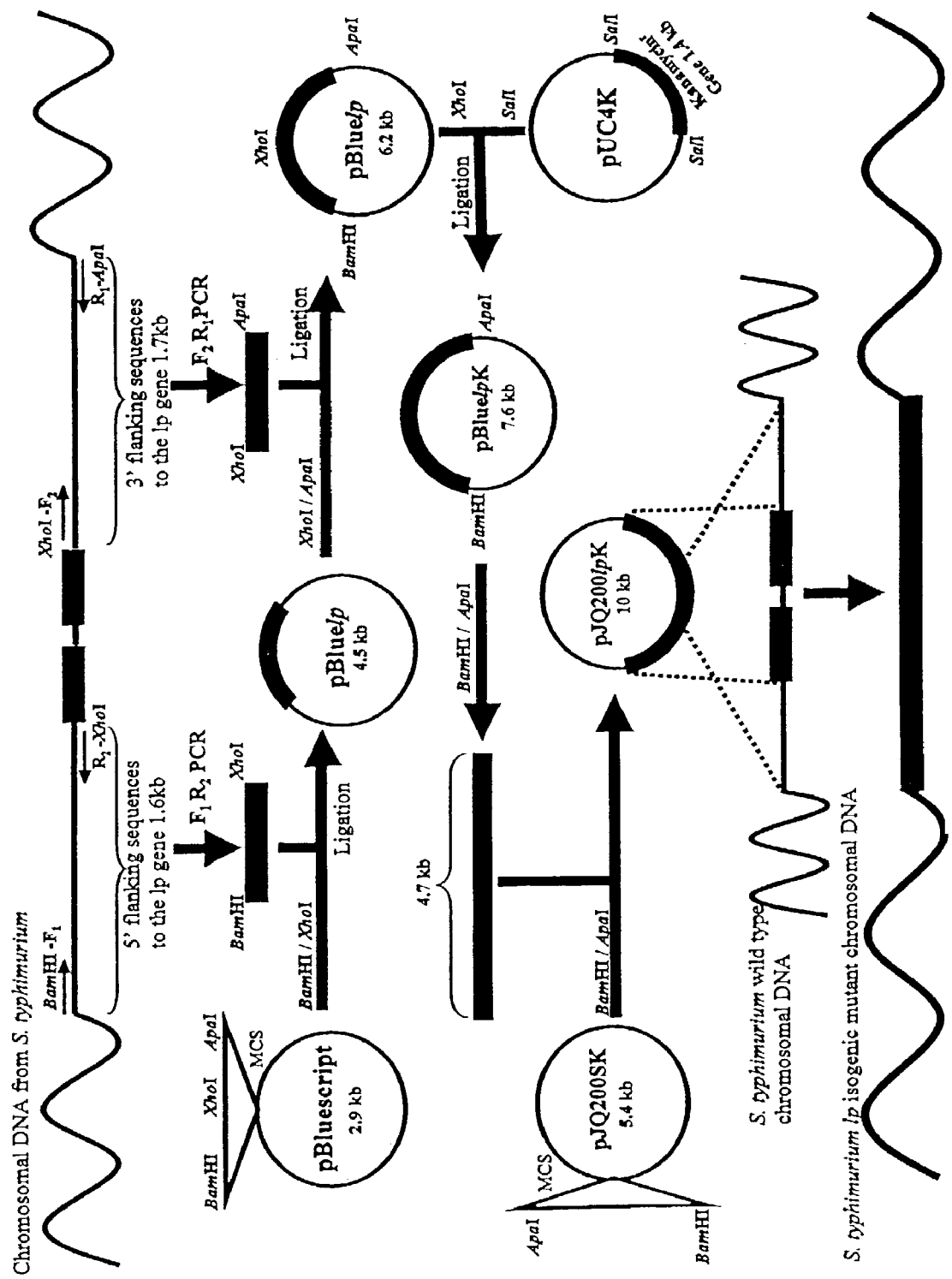
FIG. 1 illustrates a diagram showing an example of the construction of a lpp gene knockout vector for *Salmonella typhimurium*.

Embodiments of the invention include vaccines and vaccine vectors produced from attenuated bacteria of the Enterobacteriaceae family. In certain embodiments, bacteria may be attenuated by manipulating the bacteria so they lack a functional lipoprotein. Lipoprotein (LP), encoded by the lpp gene, is one of the most abundant outer membrane protein in the bacteria of the Enterobacteriaceae family. LP is an important mediator of septic shock and can induce in vivo and in vitro proinflammatory cytokine production from human and mouse macrophages. LP acts synergistically with lipopolysaccharide to induce lethal shock and proinflammatory cytokine production. Embodiments of the invention include compositions comprising and methods for making of an attenuated bacterium from the family Enterobacteriaceae with a non-functional LP for use as a vaccine or as a vaccine vector. In certain embodiments a *Salmonella typhimurium* lacking a wild type LP may be produced and used as a vaccine or vaccine vector.

The bacterial genome may be altered by genetic engineering techniques to eliminate all or part of the LP function resulting in reduction or elimination of bacterial virulence. For example, a *S. typhimurium* lpp mutant with a non-functional LP, an example of which is described below, demonstrates reduced virulence. Reduction of virulence of the mutant bacterium is indicated by the mutant bacterium having no harmful effects on mice following oral or intraperitoneal challenge. An effective immune response may be initiated in mice challenged with a bacterium with a non-functional LP, which are subsequently protected from wild type bacterium challenge. The LP protein and the lpp gene are conserved across the Enterobacteriaceae family, for example *Yersinia pestis* displays a 91% identity to Salmonella. Thus, any species of the Enterobacteriaceae may be manipulated by genetically altering the expression of the lpp gene or the function of the LP protein to produce an attenuated bacterium for use as a vaccine and/or vaccine vector of the invention.

In certain embodiments the lpp gene may be mutagenized to produce a bacteria lacking a functional LP. Lacking a functional LP as used herein encompasses the expression of mutant LP and the lack of expression of LP or any alteration that results in a LP that is not wild type. In various embodiments, the lpp gene may be mutagenized to eliminate expression of LP, by either transcriptional or translational effects. Elimination or knockout of LP expression may be effected by the deletion of all or part of the lpp gene or locus. Bacteria lacking a functional LP may be used as either a vaccine for the bacterium of choice or as a vaccine vector. The vaccine may be used to express recombinant genes or antigens for the purpose of stimulating an immune response to any antigen that would offer protection or treatment for a pathogen or disease (i.e., a vaccine vector).

Other embodiments encompass the methods of using a vaccine comprising an attenuated bacterium of the Enterobacteriaceae family to vaccinate a subject in need thereof. Other embodiments include methods of inducing an immune response against an attenuated bacterium of the Enterobacteriaceae family. In other embodiments, methods of vaccination using an attenuated bacterium of the Enterobacteriaceae family as a vaccination vector are also contemplated.

I. Enterobacteriaceae

Enterobacteriaceae is a family of gram-negative, rod-shaped, facultatively anaerobic bacteria found in soil, water, plants, and animals, which frequently occur as pathogens in vertebrates. Members of genera belonging to the Enterobacteriaceae family are among the most pathogenic and most common organisms in clinical microbiology. The bacteria of this family share a similar physiology and demonstrate a conservation within functional elements and genes of the respective genomes. Thus, the methods and compositions of the invention will typically be applicable across members of the Enterobacteriaceae family. These gram-negative rods are usually associated with intestinal infections, but can be found in almost all natural habitats. They are the causative agents of such diseases as meningitis, bacillary dysentery, typhoid, and food poisoning. As well as being oxidase negative, all members of this family are glucose fermenters and nitrate reducers. In most cases, the pathogenicity of a particular enteric bacterium can be determined by its ability to metabolize lactose. Non-utilizers are usually pathogenic while the lactose utilizers are not. The genera of the Enterobacteriaceae family that are commonly encountered in the clinical laboratory are: *Escherichia coli, Shigella, Edwardsiella, Salmonella, Citrobacter, Klebsiella, Enterobacter, Serratia, Proteus, Morganella, Providencia*, and *Yersinia*.

A. *Escherichia coli*

*Escherichia coli* (*E. coli*) is a common research tool in microbiology and genetics. *E. coli* is also the number one cause of human urinary tract infections and has been linked to numerous diseases. Diseases linked to pathogenic strains of *Escherichia coli* include pneumonia, meningitis, diarrhea, and hemolytic uremic syndrome.

B. *Shigella*

*Shigella* is closely related to *E. coli*. In many cases, a Shigella infection will lead to diarrhea accompanied by fever. *Shigella* is also an invasive pathogen (the pathogen colonizes tissues as opposed to growing on tissue surfaces). Species in this genus are sometimes designated serologically: for example, Serotype A—*S. dysenteriae*; Serotype B—*S. flexneri*; Serotype C—*S. boydii*; and Serotype D—*S. sonnei* (a common causative agent of shigellosis).

C. *Edwardsiella*

*Edwardsiella* is biochemically similar to *E. coli* with the exception that *E. tarda* produces hydrogen sulfide. Species of this bacterium are typically found in aquatic animals and reptiles. However, some species are known to cause gastroenteritis and wound infections.

D. *Salmonella*

*Salmonella* bacteria are commonly related to cases of bacterial food poisoning. Transmission of this microbe is usually through uncooked meats and eggs. Chickens are a major reservoir of *Salmonella*. Ingesting foods contaminated with significant amounts of *Salmonella* can cause intestinal infection resulting in diarrhea, vomiting, chills, and a headache. The approximately 2200 known species of *Salmonella* are classified according to their surface antigens. The capsular properties of this Gram-negative rod can cause serious complications in immunosuppressed individuals such as HIV/AIDS patients. *S. typhimurium* and *S. enteritidis* are two of the leading causes of salmonellosis (inflammation of the intestine caused by *Salmonella*). *S. typhi* is a unique species because it is only carried by humans. This intracellular parasite can cause typhoid fever (enteric fever) which is characterized by fever, diarrhea, and inflammation of the infected organs.

E. *Citrobacter*

*Citrobacter* species *C. freundii* is suspected to cause diarrhea and possibly extraintestinal infections and *C. diversus* has been linked to meningitis in newborns.

F. *Klebsiella*

*Klebsiella pneumoniae*, clinically important species of this genus, is a non-motile bacterium that produces large sticky colonies when plated on nutrient media. *Klebsiella*'s pathogenicity can be attributed to its production of a heat-stable enterotoxin. *K. pneumoniae* infections are common in hospitals where they cause pneumonia and urinary tract infections.

G. *Enterobacter*

*Enterobacter* includes eleven species of highly motile bacteria. *Enterobacter* are biochemically similar to *Klebsiella*, the key difference being that *Enterobacter* are ornithine positive. Several *Enterobacter* species cause opportunistic infections, for example infections of the urinary or respiratory tract.

H. *Serratia*

*Serratia marcescens* is known to cause urinary tract infections, wound infections, and pneumonia. *Serratia* bacteria also have many antibiotic resistance properties which may become important if the incidence of *Serratia* infections dramatically increases.

I. *Proteus*

*Proteus* may cause urinary tract infections and hospital-acquired infections. *Proteus* is unique due to it is highly motile and irregular colonies on non-inhibitory media, "swarming colonies". *Proteus mirabilis* is a cause of wound and urinary tract infections. This organism typically targets immunosuppressed subjects.

J. *Morganella*

*Morganella morganii* may cause urinary tract and wound infections, as well as diarrhea.

K. *Providencia*

*Providencia* species have been associated with hospital acquired urinary tract infections and in some cases diarrhea in children.

L. *Yersinia*

*Yersinia enterocolitica* and *Y. pestis* are two species of interest. *Y. enterocolitica* is an invasive pathogen which can penetrate the gut lining and enter the lymphatic system and the blood. Infection is usually through ingestion of contaminated foods and may cause severe intestinal inflammation (yersiniosis). Enterotoxin release may cause severe pain that mimics appendicitis. *Y. pestis* is the cause of bubonic, pneumonic, and septicemic plagues. Once infection is established, *Y. pestis* release a toxin which inhibits electron transport chain function and results in lymph node swelling, skin blotches, and delirium. Untreated infections typically result in death within a week of initial infection.

Various strains of Enterobacteriaceae may be obtained through a number of suppliers, such as the ATCC (American Type Culture Collection, 10801 University Boulevard, Manassas Va. 20110-2209, USA), DSM (Deutsche Sammlung von Mikroorganismen und Zellkulturen, Braunschweig, Germany), and NCTC (National Collection of Type Cultures, London, UK). In general, growth conditions consists of a growth media and incubation at an appropriate temperature in the approximate range of 28° C. to 37° C., typically liquid cultures are grown in a shaking incubator. For example, bacterial strains may be grown at 37° C. in Luria-Bertani (LB) medium, on LB agar, 3 Nutrient agar (Difco No. 212000, Fisher Scientific, Pittsburgh, Pa.), nutrient broth (Difco No. 233000, Fisher Scientific, Pittsburgh, Pa.), M9 minimal salts with glucose or other appropriate growth media, typically with aeration. Growth media may also be supplemented with thiamine, spectinomycin, kanamycin, chloramphenicol, penicillin or other supplements or selective agents in appropriate amounts, as required. Bacterium from overnight cultures of bacteria may be harvested by centrifugation. Growth conditions may vary and suggested growth conditions are provided by the suppliers.

Embodiments of the invention will include compositions comprising and method of making Enterobacteriaceae with a non-functional LP, wherein various embodiments include, but not limited to attenuated bacteria of the genera *Escherichia Coli, Shigella, Edwardsiella, Salmonella, Citrobacter, Klebsiella, Enterobacter, Serratia, Proteus, Erwinia, Morganella, Providencia,* or *Yersinia.*

Various embodiments include compositions comprising and methods of making Enterobacteriaceae with a non-functional LP of the species *Escherichia coli, Escherichia blattae, Escherichia fergusonii, Escherichia hermanii, Escherichia vuneris, Salmonella enterica, Salmonella typhimurium, Salmonella salamae, Salmonella arizonae, Salmonella diarizonae, Salmonella houtenae, Salmonella bongori, Salmonella indica, Shigella dysenteriae, Shigella flexneri, Shigella boydii, Shigella sonnet, Enterobacter aerogenes, Enterobacter gergoviae, Enterobacter sakazaki, Enterobacter cloacae, Enterobacter agglomerans, Klebsiella pneumoniae, Serratia marcescens, Yersinia pseudotuberculosis, Yersinia pestis, Yersinia enterocolitica, Erwinia, Proteus mirabilis, Proteus vulgaris, Proteus penneri, Proteus hauseri, Providencia alcalifaciens,* or *Morganella morganii.*

II. Lipoprotein (LP) Encoding Gene (lpp)

The lpp gene encodes the outer membrane lipoprotein in *E. coli* and other related bacterium in the family Enterobacteriaceae (Ching and Inouye, 1985). LP is one the most abundant proteins in *E. coli*. The C-terminus of the protein is frequently covalently linked to the peptidoglycan layer of the bacteria, this modification plays a role in maintenance of structural integrity. The N-terminus of the protein may contain a glyceride-modified cysteine that is involved in the processing and secretion of the protein. The lpp genes from various Enterobacteriaceae have been cloned and DNA analysis shows that the genes are highly conserved during evolution (Nakamura and Inouye, 1979; Yamagata et al., 1981; and Huang et al., 1983).

Based on amino acid and nucleic acid comparisons, the lpp gene may be divided into 6 regions: a signal peptide region and regions A-E, which are defined as regions of amino acid sequence and/or nucleotide sequence with differing degrees of conservation between species. The degree of substitution within the gene and protein define structurally and/or functionally conserved regions within the Enterobacteriaceae family. Some members of the Enterobacteriaceae may have two lpp genes in tandem. In bacteria that contain such a gene arrangement both genes will typically be deleted or mutated.

Other methods of attenuation may be used in combination with lipoprotein manipulation to produce a vaccine vector expressing a recombinant gene(s) so that a heterologous antigen is effectively presented to the host immune system. The bacteria lose in large part their virulent properties, thus allowing them to multiply in the host to a limited extent, but not enough to cause significant disease or disorder. In a certain embodiments, bacteria which reside in lymphoid tissues such as the spleen (e.g., *Salmonella* spp.) are used. Such bacteria may invade gut epithelial tissue and/or Peyer's patches, disseminate throughout the reticuloendothelial system, and gain access to mesenteric lymphoid tissue, liver and spleen, where they multiply or at least survive for a time, and induce humoral and cell-mediated immunity.

Attenuation methods that may be used in combination with the attenuation methods of the present invention include, but are not limited to chemical mutagenesis, genetic insertion, deletion (Miller, J., 1972) or recombinant DNA methodology (Maniatis, et al., 1988), laboratory selection of natural mutations, etc. Methods for obtaining attenuated *Salmonella* strains which are non-reverting non-virulent auxotrophic mutants suitable for use as live vaccines are described in U.S. Pat. Nos. 4,550,081, 4,735,801 and 4,837,151, the teachings of which are incorporated by reference herein in their entirety. A reliable method to achieve attenuation of Salmonella has also been described (Hoiseth and Stocker, 1981; Stocker et al., 1982) and can be used in particular embodiments of the invention.

Accession numbers for various lipoproteins of the family Enterobacteriaceae include, but are not limited to AAL20301, CAD01988, NP_456148, CAA23580, NP_460342, LPECW, P02937, CAA48767, AAC74747, BAA16044, NP_310411, NP_288111, AAG56664, BAB35807, NPWCWY, P02939, AAA24824, CAC91199, NP_405930, CAA24640, LPSEW, P02938, AAA26566, CAD01989, NP_456149, AAL20300, NP_460341, LPEBWM, P02940, AAA25322, A24352, AAA25658, AAA25659, D65088, AAB 22836, and P09461 (all of which are incorporated herein by reference).

Accession numbers for various nucleic acids encoding lipoproteins of the family Enterobacteriaceae include, but are not limited to AE008760, V00302, D63765, AL627271, X68953, and the like (all of which are incorporated by reference).

III. Vaccines

The present invention includes methods of inducing the immune response in a subject by contacting the subject with an Enterobacteriaceae antigenic composition, wherein the antigen comprises an attenuated bacterium, a bacterially expressed heterologous antigenic epitope, or an attenuated bacterium with an antigen on the cell surface. As used herein, an "antigenic composition" may comprise an attenuated bacterium of the Enterobacteriaceae family, an antigen (e.g., a peptide or polypeptide), a nucleic acid encoding an antigen (e.g., an antigen expression vector), or a cell expressing or presenting an antigen.

In one embodiment of the present invention, an expression vector encoding a heterologous antigen is transferred into an attenuated bacterium, where it is expressed, thus producing a bacterial strain suitable for use as a live vaccine. In particular embodiments the bacterium is attenuated by manipulation of lipoprotein expression. In other embodiments, alternative means of attenuation may be used in combination with lipoprotein deficient bacterium.

In other embodiments, the antigenic composition is in a mixture that comprises an additional immunostimulatory agent or nucleic acids encoding such an agent. Immunostimulatory agents include but are not limited to an additional antigen, an immunomodulator, an antigen presenting cell or an adjuvant. In other embodiments, one or more of an additional agent is coupled to an attenuated Enterobacteriaceae bacterium, an antigen or an agent, preferably an antigen or agent is covalently coupled to an attenuated bacterium.

In certain embodiments, the antigenic composition is administered to an animal, the animal may be a human patient infected or exposed to pathogenic agent and more preferably a human patient infected or exposed to a bacterial pathogen. In other embodiments the animal is a human cancer patient, a human breast cancer patient, a human prostate cancer patient, human leukemia patient or a human melanoma patient.

A. Immune Response

The immune response is the way the body defends itself against microorganisms, cancer cells, and other potentially harmful substances or organisms. Antigens are typically molecules (usually proteins) on the surface of cells, viruses, fungi, bacteria, and some non-living substances such as toxins, chemicals, drugs, and foreign particles. The immune system recognizes and destroys substances containing these antigens.

The immune response may be an active immune response. Alternatively, the response may be part of an adoptive immunotherapy approach in which lymphocyte(s) are obtained from an animal (e.g., a patient), then pulsed with composition comprising an antigenic composition. In this embodiment, the antigenic composition may comprise an additional immunostimulatory agent or a nucleic acid encoding such an agent. The lymphocyte(s) may be obtained from the blood of the subject, or alternatively from tumor tissue to obtain tumor infiltrating lymphocyte(s) as disclosed in Rosenberg et al, 1986, incorporated herein by reference. In certain preferred embodiments, the lymphocyte(s) are peripheral blood lymphocyte(s). In one embodiment, the lymphocyte(s) are administered to the same or different animal (e.g., same or different donors). In a another embodiment, the animal (e.g., a patient) has or is suspected of having a cancer, such as for example, a breast or prostate cancer. In other embodiments the method of enhancing the immune response is practiced in conjunction with a cancer therapy, such as for example, a cancer vaccine therapy.

Active immunity develops when the body is exposed to various antigens (antigenic epitopes). It involves lymphocytes, of which there are 2 main groups, B lymphocytes and T lymphocytes. B lymphocytes (also called B cells) produce antibodies. Antibodies attach to a specific antigen and make it easier for the phagocytes to destroy the antigen. T lymphocytes (T cells) attack antigens directly, and some T lymphocytes provide control of the immune response. B cells and T cells develop that are specific for an antigen type. When you are exposed to a different antigen, different B cells and T cells are formed.

1. B Cells

B cells are a type of lymphocyte. The B cell produces antibodies that bind antigens. Each B cell is programmed to make a specific antibody. When a B cell encounters its antigen (along with collaborating T cells and accessory cells), it gives rise to many large plasma cells. Every plasma cell is a factory for producing antibody. Each of the plasma cells descended from a given B cell (which are all members of the same family, or clone) manufactures millions of identical antibody molecules and pours them into the bloodstream.

A given antibody has an affinity for a particular antigen. The antibody-antigen interaction marks the antigen or the cell displaying the antigen for destruction. After the human body has recovered from a disease, B-cells produce memory cells that attack the disease causing organism if it invades again. This second response is much quicker than the first, thus preventing symptoms of the disease from occurring. Development of memory B cells and effector B cells (plasma cells) occurs in two phases. Short-lived plasma cells that make mostly IgM (but some IgG) are generated during the primary response and occupy sites, such as the splenic red pulp or lymph node medulla. The second phase involves the formation of the memory B-cell pool and seeding of long-lived plasma cells to the bone marrow. Plasma cells are terminally differentiated and do not give rise to memory cells.

Development of memory T cells (CD4 and CD8) may occur after activation, cells differentiate into effector T cells. Memory T cells may be generated from effector T cells. There may be two subsets of memory cells: quiescent, central memory cells that recirculate from blood to secondary lymphoid organs, and effector memory cells that migrate through tissues and deliver a very rapid response on reactivation with antigen.

2. Cytotoxic T Lymphocytes

In certain embodiments, T-lymphocytes are activated by contact with an antigen presenting cell that is in contact with an antigen of the invention.

T cells express a unique antigen binding receptor on their membrane (T-cell receptor), which can only recognize antigen in association with major histocompatibility complex (MHC) molecules on the surface of other cells. There are several populations of T cells, such as T helper cells and T cytotoxic cells. T helper cells and T cytotoxic cells are primarily distinguished by their display of the membrane bound glycoproteins CD4 and CD8, respectively. T helper cells secrete various lymphokines, that are crucial for the activation of B cells, T cytotoxic cells, macrophages and other cells of the immune system. In contrast, a T cytotoxic cell that recognizes an antigen-MHC complex proliferates and differentiates into an effector cell called a cytotoxic T lymphocyte (CTL). CTLs eliminate cells of the body displaying antigen, such as virus infected cells and tumor cells, by producing substances that result in cell lysis.

CTL activity can be assessed by methods described herein or as would be known to one of skill in the art. For example, CTLs may be assessed in freshly isolated peripheral blood mononuclear cells (PBMC), in a phytohaemaglutinin-stimulated IL-2 expanded cell line established from PBMC (Bernard et al., 1998) or by T cells isolated from a previously immunized subject and restimulated for 6 days with dendritic cells infected with an adenovirus vector containing antigen using standard 4 hr $^{51}$Cr release microtoxicity assays. One type of assay uses cloned T-cells. Cloned T-cells have been tested for their ability to mediate both perforin and Fas ligand-dependent killing in redirected cytotoxicity assays (Simpson et al., 1998). The cloned cytotoxic T lymphocytes displayed both Fas- and perforin-dependent killing. Recently, an in vitro dehydrogenase release assay has been developed that takes advantage of a new fluorescent amplification system (Page et al., 1998). This approach is sensitive, rapid, reproducible and may be used advantageously for mixed lymphocyte reaction (MLR). It may easily be further automated for large scale cytotoxicity testing using cell membrane integrity, and is thus considered in the present invention. In another fluorometric assay developed for detecting cell-mediated cytotoxicity, the fluorophore used is the non-toxic molecule alamarBlue (Nociari et al., 1998). The alamarBlue is fluorescently quenched (i.e., low quantum yield) until mitochondrial reduction occurs, which then results in a dramatic increase in the alamarBlue fluorescence intensity (i.e., increase in the quantum yield). This assay is reported to be extremely sensitive, specific and requires a significantly lower number of effector cells than the standard $^{51}$Cr release assay.

In certain aspects, T helper cell responses can be measured by in vitro or in vivo assay with peptides, polypeptides or proteins. In vitro assays include measurement of a specific cytokine release by enzyme, radioisotope, chromaphore or fluorescent assays. In vivo assays include delayed type hypersensitivity responses called skin tests, as would be known to one of ordinary skill in the art.

3. Antigen Presenting Cells

In general, the term "antigen presenting cell" can be any cell that accomplishes the goal of the invention by aiding the enhancement of an immune response (i.e., from the T-cell or -B-cell arms of the immune system) against an antigenic composition of the present invention or a heterologous antigen or a immunologically functional equivalent. Such cells can be defined by those of skill in the art, using methods disclosed herein and in the art. As is understood by one of ordinary skill in the art and used herein certain embodiments, a cell that displays or presents an antigen normally or preferentially with a class II major histocompatibility molecule or complex to an immune cell is an "antigen presenting cell." In certain aspects, a cell (e.g., an APC cell) may be fused with another cell, such as a recombinant cell or a tumor cell that expresses the desired antigen. Methods for preparing a fusion of two or more cells is well known in the art, such as for example, the methods disclosed in Goding, pp. 65-66, 71-74, 1986; Campbell, pp. 75-83, 1984; Kohler and Milstein, 1975; Kohler and Milstein, 1976, Gefter et al., 1977, each incorporated herein by reference. In some cases, the immune cell to which an antigen presenting cell displays or presents an antigen to is a CD4+TH cell. Additional molecules expressed on the APC or other immune cells may aid or improve the enhancement of an immune response. Secreted or soluble molecules, such as for example, cytokines and adjuvants, may also aid or enhance the immune response against an antigen. Such molecules are well known to one of skill in the art, and various examples are described herein.

The dendritic cell (DC) is the cell type best suited for vaccine antigen delivery, as they are the most potent antigen presenting cells, effective in the stimulation of both primary and secondary immune responses (Steinman, 1999; Celluzzi and Falo, 1997). It is contemplated in the present invention that the exposure of dendritic cells with a bacterial vaccine vector of the invention, will elicit a potent immune response specific for the vaccine or vaccine vector of the present invention.

B. Vaccine Vectors

An attenuated bacterium of the Enterobacteriaceae family may be generated which encodes and expresses a heterologous antigen. The heterologous antigen encoded by an attenuated bacterium of the Enterobacteriaceae family is one which when expressed by the attenuated bacteria is capable of inducing an immune response and providing protection and/or therapy in an animal against challenge by an infectious agent from which the heterologous antigen was derived, or which is capable of affecting tumor growth and metastasis in a manner which is of benefit to a host organism. Heterologous antigens which may be introduced into an attenuated bacterium of the Enterobacteriaceae family by way of DNA encoding the same thus include any antigen which when expressed by attenuated gram-negative bacteria serves to elicit a cellular immune response which is of benefit to the host in which the response is induced. Heterologous antigens therefore include those specified by infectious agents, wherein an immune response directed against the antigen serves to prevent or treat disease caused by the agent. Such heterologous antigens include, but are not limited to, viral, bacterial, fungal or parasite surface proteins and any other proteins, glycoproteins, lipoprotein, glycolipids, and the like.

Heterologous antigens also include those which provide benefit to a host organism which is at risk for acquiring or which is diagnosed as having a tumor. The host organism in certain embodiments is a vertebrate. In other embodiments the host organism is a mammal. In particular embodiments the host organism is a human. Other host organisms include, but are not limited to domestic animals (e.g. cats, dogs, birds, and the like), farm animals (e.g. chickens, fowl, cows, horses, goats, pigs, and the like) and wildlife (e.g. deer, bison, and the like).

C. Nucleic Acid Compositions

Certain embodiments of the present invention concern an attenuated bacterium comprising an expression vector encoding an antigen. In certain aspects, an expression vector comprises a nucleic acid encoding whole or partial, wild-type or mutant antigen. In particular aspects, a nucleic acid encodes for or comprises a transcribed nucleic acid. In particular aspects, a nucleic acid encodes a protein, a polypeptide, or a peptide.

The term "nucleic acid" is well known in the art. A "nucleic acid" as used herein will generally refer to a molecule (i.e., a strand) of DNA or RNA. A nucleobase includes, for example, a naturally occurring purine or pyrimidine base found in DNA (e.g., an adenine "A," a guanine "G," a thymine "T" or a cytosine "C") or RNA (e.g., an A, a G, an uracil "U" or a C). The term "nucleic acid" encompasses the terms "oligonucleotide" and "polynucleotide," each as a subgenus of the term "nucleic acid." The term "oligonucleotide" refers to a molecule of between about 3 and about 100 nucleobases in length. The term "polynucleotide" refers to at least one molecule of greater than about 100 nucleobases in length.

These definitions generally refer to a single-stranded molecule, but in specific embodiments will also encompass an additional strand that is partially, substantially or fully complementary to the single-stranded molecule. Thus, a nucleic acid may encompass a double-stranded molecule or a triple-stranded molecule that comprises one or more complementary strand(s) or "complement(s)" of a particular sequence comprising a molecule. As used herein, a single stranded nucleic acid may be denoted by the prefix "ss," a double stranded nucleic acid by the prefix "ds," and a triple stranded nucleic acid by the prefix "ts."

1. Nucleobases

As used herein a "nucleobase" refers to a heterocyclic base, such as for example a naturally occurring nucleobase (i.e., an A, T, G, C or U) found in at least one naturally occurring nucleic acid (i.e., DNA and RNA), and naturally occurring derivative(s) of such a nucleobase. A nucleobase generally can form one or more hydrogen bonds ("anneal" or "hybridize") with at least one naturally occurring nucleobase (e.g., hydrogen bonding between A and T, G and C, and A and U).

"Purine" and/or "pyrimidine" nucleobase(s) encompass naturally occurring purine and/or pyrimidine nucleobases. A nucleobase may be comprised in a nucleside or nucleotide, using any chemical or natural synthesis method described herein or known to one of ordinary skill in the art.

2. Nucleosides

As used herein, a "nucleoside" refers to an individual chemical unit comprising a nucleobase covalently attached to a nucleobase linker moiety. A non-limiting example of a "nucleobase linker moiety" is a sugar comprising 5-carbon atoms (i.e., a "5-carbon sugar"), including but not limited to a deoxyribose, a ribose, or an arabinose.

Different types of covalent attachment(s) of a nucleobase to a nucleobase linker moiety are known in the art. By way of non-limiting example, a nucleoside comprising a purine (i.e., A or G) or a 7-deazapurine nucleobase typically covalently attaches the 9 position of a purine or a 7-deazapurine to the 1'-position of a 5-carbon sugar. In another non-limiting example, a nucleoside comprising a pyrimidine nucleobase (i.e., C, T or U) typically covalently attaches a 1 position of a pyrimidine to a 1'-position of a 5-carbon sugar (Kornberg and Baker, 1992).

3. Nucleotides

As used herein, a "nucleotide" refers to a nucleoside further comprising a "backbone moiety". A backbone moiety generally covalently attaches a nucleotide to another molecule comprising a nucleotide, or to another nucleotide to form a nucleic acid. The "backbone moiety" in naturally occurring nucleotides typically comprises a phosphorus moiety, which is covalently attached to a 5-carbon sugar. The attachment of the backbone moiety typically occurs at either the 3'- or 5'-position of the 5-carbon sugar.

4. Preparation of Nucleic Acids

A nucleic acid may be made by any technique known to one of ordinary skill in the art, such as for example, chemical synthesis, enzymatic production or biological production. Non-limiting examples of a synthetic nucleic acid (e.g., a synthetic oligonucleotide), include a nucleic acid made by in vitro chemically synthesis using phosphotriester, phosphite or phosphoramidite chemistry and solid phase techniques such as described in EP 266,032, incorporated herein by reference, or via deoxynucleoside H-phosphonate intermediates as described by Froehler et al., 1986 and U.S. Pat. No. 5,705,629, each incorporated herein by reference. In the methods of the present invention, one or more oligonucleotide may be used. Various different mechanisms of oligonucleotide synthesis have been disclosed in for example, U.S. Pat. Nos. 4,659,774, 4,816,571, 5,141,813, 5,264,566, 4,959, 463, 5,428,148, 5,554,744, 5,574,146, and 5,602,244, each of which is incorporated herein by reference.

A non-limiting example of an enzymatically produced nucleic acid includes one produced by enzymes in amplification reactions such as PCR™ (see for example, U.S. Pat. No. 4,683,202 and U.S. Pat. No. 4,682,195, each incorporated herein by reference), or the synthesis of an oligonucleotide described in U.S. Pat. No. 5,645,897, incorporated herein by reference. A non-limiting example of a biologically produced nucleic acid includes a recombinant nucleic acid produced (i.e., replicated) in a living cell, such as a recombinant DNA vector replicated in bacteria (see for example, Sambrook et al 1989, incorporated herein by reference).

5. Purification of Nucleic Acids

A nucleic acid may be purified on polyacrylamide gels, cesium chloride centrifugation gradients, or by any other means known to one of ordinary skill in the art (see for example, Sambrook et al., 1989, incorporated herein by reference).

In certain aspect, the present invention concerns a nucleic acid that is an isolated nucleic acid. As used herein, the term "isolated nucleic acid" refers to a nucleic acid molecule (e.g., an RNA or DNA molecule) that has been isolated free of, or is otherwise free of, the bulk of the total genomic and transcribed nucleic acids of one or more cells. In certain embodiments, "isolated nucleic acid" refers to a nucleic acid that has been isolated free of, or is otherwise free of, bulk of cellular components or in vitro reaction components such as for example, macromolecules such as lipids or proteins, small biological molecules, and the like.

6. Nucleic Acid Segments

In certain embodiments, the nucleic acid is a nucleic acid segment. As used herein, the term "nucleic acid segment," are smaller fragments of a nucleic acid, such as for non-limiting example, those that encode only part of antigenic peptide or polypeptide sequence. Thus, a "nucleic acid segment" may comprise any part of a gene sequence, of from about 2 nucleotides to the full length of an antigenic peptide or polypeptide encoding region.

Various nucleic acid segments may be designed based on a particular nucleic acid sequence, and may be of any length. By assigning numeric values to a sequence, for example, the first residue is 1, the second residue is 2, etc., an algorithm defining all nucleic acid segments can be created:

n to n+y where n is an integer from 1 to the last number of the sequence and y is the length of the nucleic acid segment minus one, where n+y does not exceed the last number of the sequence. Thus, for a 10-mer, the nucleic acid segments correspond to bases 1 to 10, 2 to 11, 3 to 12 . . . and so on. For a 15-mer, the nucleic acid segments correspond to bases 1 to 15, 2 to 16, 3 to 17 . . . and so on. For a 20-mer, the nucleic segments correspond to bases 1 to 20, 2 to 21, 3 to 22 . . . and so on. In certain embodiments, the nucleic acid segment may be a probe or primer. As used herein, a "probe" generally refers to a nucleic acid used in a detection method or composition. As used herein, a "primer" generally refers to a nucleic acid used in an extension or amplification method or composition.

7. Hybridization

As used herein, "hybridization", "hybridizes" or "capable of hybridizing" is understood to mean the forming of a double or triple stranded molecule or a molecule with partial double or triple stranded nature. The term "anneal" as used herein is synonymous with "hybridize." The term "hybridization", "hybridize(s)" or "capable of hybridizing" encompasses the terms "stringent condition(s)" or "high stringency" and the terms "low stringency" or "low stringency condition(s)."

As used herein "stringent condition(s)" or "high stringency" are those conditions that allow hybridization between or within one or more nucleic acid strand(s) containing complementary sequence(s), but precludes hybridization of random sequences. Stringent conditions tolerate little, if any, mismatch between a nucleic acid and a target strand. Such conditions are well known to those of ordinary skill in the art, and are preferred for applications requiring high selectivity. Non-limiting applications include isolating a nucleic acid, such as a gene or a nucleic acid segment thereof, or detecting at least one specific mRNA transcript or a nucleic acid segment thereof, and the like.

Stringent conditions may comprise low salt and/or high temperature conditions, such as provided by about 0.02 M to about 0.15 M NaCl at temperatures of about 50° C. to about 70° C. It is understood that the temperature and ionic strength of a desired stringency are determined in part by the length of the particular nucleic acid(s), the length and nucleobase content of the target sequence(s), the charge composition of the nucleic acid(s), and to the presence or concentration of formamide, tetramethylammonium chloride or other solvent(s) in a hybridization mixture.

It is also understood that these ranges, compositions and conditions for hybridization are mentioned by way of non-limiting examples only, and that the desired stringency for a particular hybridization reaction is often determined empirically by comparison to one or more positive or negative controls. Depending on the application envisioned it is preferred to employ varying conditions of hybridization to achieve varying degrees of selectivity of a nucleic acid towards a target sequence. In a non-limiting example, identification or isolation of a related target nucleic acid that does not hybridize to a nucleic acid under stringent conditions may be achieved by hybridization at low temperature and/or high ionic strength. Such conditions are termed "low stringency" or "low stringency conditions", and non-limiting examples of low stringency include hybridization performed at about 0.15 M to about 0.9 M NaCl at a temperature range of about 20° C. to about 50° C. Of course, it is within the skill of one in the art to further modify the low or high stringency conditions to suite a particular application.

As used herein "wild-type" refers to the naturally occurring sequence of a nucleic acid at a genetic locus in the genome of an organism, or a sequence transcribed or translated from such a nucleic acid. Thus, the term "wild-type" also may refer to an amino acid sequence encoded by a nucleic acid. As a genetic locus may have more than one sequence or alleles in a population of individuals, the term "wild-type" encompasses all such naturally occurring allele(s). As used herein the term "polymorphic" means that variation exists (i.e., two or more alleles exist) at a genetic locus in the individuals of a population. As used herein "mutant" refers to a change in the sequence of a nucleic acid or its encoded protein, polypeptide or peptide that is the result of the hand of man.

The present invention also concerns the isolation or creation of a recombinant construct or a recombinant host cell through the application of recombinant nucleic acid technology known to those of skill in the art or as described herein. A recombinant construct or host cell may comprise an antigen encoding nucleic acid, a homologous recombination cassette or a combination thereof. An antigen encoding nucleic acid may express a heterologous protein, polypeptide or peptide, or at least one biologically functional equivalent thereof. A homologous recombination cassette may be intergrated into the genome to effect the removal, replacement, substitution, addition, or alteration of genomic nucleic acid sequences.

Herein, a "gene" refers to a nucleic acid that is transcribed. In certain aspects, the gene includes regulatory sequences involved in transcription, or message production or composition. In particular embodiments, the gene comprises transcribed sequences that encode for a protein, polypeptide or peptide. As will be understood by those in the art, this functional term "gene" includes both genomic sequences, RNA or cDNA sequences or smaller engineered nucleic acid segments, including nucleic acid segments of a non-transcribed part of a gene, including but not limited to the non-transcribed promoter or enhancer regions of a gene. Smaller engineered gene nucleic acid segments may express, or may be adapted to express using nucleic acid manipulation technology, proteins, polypeptides, domains, peptides, fusion proteins, mutants and/or the like.

"Isolated substantially away from other coding sequences" means that the gene of interest forms the significant part of the coding region of the nucleic acid, or that the nucleic acid does not contain large portions of naturally-occurring coding nucleic acids, such as large chromosomal fragments, other functional genes, RNA or cDNA coding regions. Of course, this refers to the nucleic acid as originally isolated, and does not exclude genes or coding regions later added to the nucleic acid by the hand of man.

The nucleic acid(s) of the present invention, regardless of the length of the sequence itself, may be combined with other nucleic acid sequences, including but not limited to, promoters, enhancers, polyadenylation signals, restriction enzyme sites, multiple cloning sites, coding segments, and the like, to create one or more nucleic acid construct(s). As used herein, a "nucleic acid construct" is a nucleic acid engineered or altered by the hand of man, and generally comprises one or more nucleic acid sequences organized by the hand of man.

In some embodiments, a nucleotide may involve 1, 2, 3, 4, 5, 6, 7, 8, 9, 10, 15, 20, 30, 40, 50, 60, 70, 80, 90, 100, 110, 120, 130, 140, 150, 160, 170, 180, 190, 200, 250, 300, 350, 400, 450, 500, 550, 600, 650, 700, 750, 800, 850, 900, 950, 1000 or more continuous nucleotides, or at least or at most that many nucleotides of an lpp gene (e.g., SEQ ID NO: 1, 3, or 5). In other embodiments all or part of the nucleotide sequences of SEQ ID NO:1, 3, and/or 5 may be deleted from the genome of a target bacterium.

In a non-limiting example, one or more nucleic acid constructs may be prepared that include a contiguous stretch of nucleotides identical to or complementary to SEQ ID NO: 1, 3, or 5. A nucleic acid construct may be about 3, about 5, about 8, about 10 to about 14, or about 15, about 20, about 30, about 40, about 50, about 100, about 200, about 500, about 1,000, about 2,000, about 3,000, about 5,000, about 10,000, about 15,000, about 20,000, about 30,000, about 50,000, about 100,000, about 250,000, about 500,000, about 750,000, to about 1,000,000 nucleotides in length, as well as constructs of greater size, up to and including chromosomal sizes (including all intermediate lengths and intermediate ranges), given the advent of nucleic acids constructs such as a yeast artificial chromosome are known to those of ordinary skill in the art. It will be readily understood that "intermediate lengths" and "intermediate ranges", as used herein, means any length or range including or between the quoted values (i.e., all integers including and between such values). Non-limiting examples of intermediate lengths include about 11, about 12, about 13, about 16, about 17, about 18, about 19, etc.; about 21, about 22, about 23, etc.; about 31, about 32, etc.; about 51, about 52, about 53, etc.; about 101, about 102, about 103, etc.; about 151, about 152, about 153, etc.; about 1,001, about 1002, etc.; about 50,001, about 50,002, etc; about 750,001, about 750, 002, etc.; about 1,000,001, about 1,000,002, etc. Non-limiting examples of intermediate ranges include about 3 to about 32, about 150 to about 500,001, about 3,032 to about 7,145, about 5,000 to about 15,000, about 20,007 to about 1,000, 003, etc.

In particular embodiments, the invention concerns one or more recombinant vector(s) comprising nucleic acid sequences that encode an antigenic protein, polypeptide or peptide. In other embodiments, the invention concerns recombinant vector(s) comprising nucleic acid sequences that encode a fusion protein, polypeptide or peptide. In particular aspects, the recombinant vectors are DNA vectors.

The term "functionally equivalent codon" is used herein to refer to codons that encode the same amino acid, such as the six codons for arginine and serine, and also refers to codons that encode biologically equivalent amino acids. For optimization of expression in bacterium of Enterobacteriaceae the codon preferences for members of the Enterobacteriaceae family, as described in Ching and Inouye, 1985, which is incorporated herein by reference, may be extrapolated and applied to nucleic acids encoding heterologous antigens of the present invention. Furthermore, codon usage for various organisms and organelles can be found at the website through world wide web at kazusa.or.jp/codon/, incorporated herein by reference, allowing one of skill in the art to optimize codon usage for expression in various organisms, particularly bacterium of the Enterobacteriaceae family, using the disclosures herein. Thus, it is contemplated that codon usage may be optimized for other prokaryotes based on the preferred codon usage as would be known to those of ordinary skill in the art.

Fusion proteins, polypeptides or peptides may be prepared, e.g., where coding regions of an antigen are aligned within the same expression unit with other proteins, polypeptides or peptides having desired functions, such as localization to a cell surface. Non-limiting examples of such desired functions of expression sequences include localization, purification or immunodetection of the added expression sequences, e.g., proteinaceous compositions that may be expressed on the cell surface, purified by affinity chromatography or the enzymatic labeling of coding regions, respectively.

Encompassed by the invention are nucleic acid sequences encoding relatively small peptides or fusion peptides, such as, for example, peptides of from about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, to about 100 amino acids in length, or more preferably, of from about 15 to about 30 amino acids in length and also larger polypeptides up to and including proteins corresponding to the full-length sequences, such as those in SEQ ID NO:2, 4, 6, 7 or 8.

As used herein an "organism" may be a prokaryote, eukaryote, virus and the like. As used herein the term "sequence" encompasses both the terms "nucleic acid" and "proteinaceous" or "proteinaceous composition." As used herein, the term "proteinaceous composition" encompasses the terms "protein", "polypeptide" and "peptide." As used herein "artificial sequence" refers to a sequence of a nucleic acid not derived from sequence naturally occurring at a genetic locus, as well as the sequence of any proteins, polypeptides or peptides encoded by such a nucleic acid. A "synthetic sequence", refers to a nucleic acid or proteinaceous composition produced by chemical synthesis in vitro, rather than enzymatic production in vitro (i.e., an "enzymatically produced" sequence) or biological production in vivo (i.e., a "biologically produced" sequence).

The DNA segments used in the present invention encompass antigens and/or biologically non-functional LP proteins and peptides. Alternatively, non-functional LP proteins or peptides may be created via the application of recombinant DNA technology, in which changes in the protein or gene structure may be engineered, based on considerations of the properties of the amino acids or nucleic acids being changed. Changes designed by man may be introduced through the application of site-directed, insertional, or deletion mutagenesis techniques, e.g., to introduce non-functional mutation in order to attenuate a target bacteria, improve the immunogenicity of an antigen, or to reduce the toxicity of an antigen.

D. Polypeptides

Polypeptides of the invention include antigens and bacterial lipoproteins, as described herein.

1. Functional Aspects

When the present application refers to the function or activity of an antigen, or "wild-type antigenic polypeptide", it is meant that the molecule in question has the ability to stimulate an immune response to the antigen, organism, particle, or substance that contains the antigen or similar structures. Other functions or activity associated with an antigen include both prophylactic or therapeutic vaccination or immunization, protection or treatment of an infection, protection against a pathogenic organism, treatment of a pathogen infection and the like. When the present application refers to the function or activity of a lipoprotein, or "wild-type lipoprotein", it is meant that the molecule in question is a naturally occurring form of lipoprotein as expressed by a bacterium of interest. A modified, mutant, or altered lipoprotein, as described herein, is a protein that has at least a one amino acid difference as compared to the wild-type lipoprotein and reduces, attenuates, or eliminates the virulence of a bacteria of interest. Determination of which molecules possess these activities may be achieved using assays familiar to those of skill in the art. For example, transfer of genes encoding an antigen, or variants thereof, into organisms may identify by, virtue of a biologic response, those molecules having an antigenic function. An endogenous antigenic polypeptide refers to the polypeptide encoded by a pathogen's genomic DNA or physical structure.

2. Polypeptide Variants

Amino acid sequence variants of a polypeptide can be substitutional, insertional or deletion variants. Deletion variants lack one or more residues of the native protein. Another common type of deletion variant is one lacking secretory signal sequences or signal sequences directing a protein to a particular part of a cell. Insertional mutants typically involve the addition of material at a non-terminal point in the polypeptide. This may include the insertion of an immunoreactive epitope, peptide or simply a single residue. Terminal additions, called fusion proteins, are discussed below.

Substitutional variants typically contain the exchange of one amino acid for another at one or more sites within the protein, and may be designed to modulate one or more properties of the polypeptide, such as stability against proteolytic cleavage, without the loss of other functions or properties. Substitutions of this kind preferably are conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

The term "biologically functional equivalent" is well understood in the art and is further defined in detail herein. Accordingly, sequences that have between about 70% and about 80%; or more preferably, between about 81% and about 90%; or even more preferably, between about 91% and about 99%; of amino acids that are identical or functionally equivalent to the amino acids of an antigenic polypeptide provided the biological activity or immunogenicity of the protein is maintained.

The term "functionally equivalent codon" is used herein to refer to codons that encode the same amino acid, such as the six codons for arginine or serine, and also refers to codons that encode biologically equivalent amino acids (see Table 1, below).

TABLE 1

CODON TABLE

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |

TABLE 1-continued

CODON TABLE

| Amino Acids | | | Codons | | | | | |
|---|---|---|---|---|---|---|---|---|
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

It also will be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned or the reduction, attenuation, or elimination of virulence where a lipoprotein is concerned.

The following is a discussion based upon changing of the amino acids of a protein to create an equivalent or an improved, second-generation molecule, as well as a protein lacking certain characteristics. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity or immunogenicity, certain amino acid substitutions can be made in a protein sequence, and in its underlying DNA coding sequence, and nevertheless produce a protein with like properties. It is thus contemplated by the inventors that various changes may be made in the DNA sequences of genes without appreciable loss of their biological utility or activity, as discussed below. Table 1 shows the codons that encode particular amino acids.

In making such changes, the hydropathic index of amino acids may be considered. The importance of the hydropathic amino acid index in conferring interactive biologic function on a protein is generally understood in the art (Kyte & Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine *−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still produce a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

Another embodiment for the preparation of polypeptides according to the invention is the use of peptide mimetics. Mimetics are peptide-containing molecules that mimic elements of protein secondary structure. See, e.g., Johnson (1993). The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used, in conjunction with the principles outline above, to engineer second generation molecules having many of the natural properties of an antigen, but with altered and even improved characteristics.

3. Fusion Proteins

A specialized kind of insertional variant is the fusion protein. This molecule generally has all or a substantial portion of the native molecule, linked at the N- or C-terminus, to all or a portion of a second polypeptide. For example, fusions typically employ leader sequences from other species to permit the recombinant expression of a protein in a heterologous host. Another useful fusion includes the addition of an immunologically active domain, such as an antibody epitope, to facilitate purification of the fusion protein. Inclusion of a cleavage site at or near the fusion junction will facilitate removal of the extraneous polypeptide after purification. Other useful fusions include linking of functional domains, such as active sites from enzymes such as a hydrolase, glycosylation domains, cellular targeting signals or transmembrane regions.

4. Protein Purification

It may be desirable to purify an antigen or variants thereof. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

Certain aspects of the present invention concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (e.g., alter pH, ionic strength, and temperature.).

A particular type of affinity chromatography useful in the purification of carbohydrate containing compounds is lectin affinity chromatography. Lectins are a class of substances that bind to a variety of polysaccharides and glycoproteins. Lectins are usually coupled to agarose by cyanogen bromide. Conconavalin A coupled to Sepharose was the first material of this sort to be used and has been widely used in the isolation of polysaccharides and glycoproteins other lectins that include lentil lectin, and wheat germ agglutinin which have been useful in the purification of N-acetyl glucosaminyl residues and *Helix pomatia* lectin, respectively. Lectins themselves are purified using affinity chromatography with carbohydrate ligands. Lactose has been used to purify lectins from castor bean and peanuts; maltose has been useful in extracting lectins from lentils and jack bean; N-acetyl-D galactosamine is used for purifying lectins from soybean; N-acetyl glucosaminyl binds to lectins from wheat germ; D-galactosamine has been used in obtaining lectins from clams and L-fucose will bind to lectins from lotus.

The matrix should be a substance that itself does not adsorb molecules to any significant extent and that has a broad range of chemical, physical and thermal stability. The ligand should be coupled in such a way as to not affect its binding properties. The ligand also should provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below.

E. Nucleic Acid-Based Expression Systems

1. Vectors

The term "vector", as used in the context genetic engineering or expression vectors, is used to refer to a carrier nucleic acid molecule into which a nucleic acid sequence can be inserted for introduction into a cell where it can be replicated. A nucleic acid sequence can be "exogenous" or "heterologous", which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques (see, for example, Maniatis et al., 1988 and Ausubel et al., 1994, both incorporated herein by reference).

The term "expression vector" refers to any type of genetic construct comprising a nucleic acid coding for a RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well and are described herein.

Successful expression of a cloned gene requires sufficient transcription of DNA, translation of the mRNA, and in some instances, post-translational modification of the protein. Expression vectors have been used to express genes under the control of an active promoter in a suitable host, and to increase protein production.

Various regulatory expression elements can be used, which are any of a number of suitable transcription and translation elements that are active in bacteria. For instance, promoters which may be used to direct the expression of the recombinant gene sequence include but are not limited to the lactose operon promoter of *E. coli*, the hybrid trp-lac UV-5 promoter (tac) (DeBoer, et al., 1982, incorporated herein by reference), the leftward (PL) and the rightward (PR) promoters of bacteriophage lambda, bacteriophage T7 promoters, the trp operon promoter, the lpp promoter (*E. coli* lipoprotein gene promoter; Nakamura and Inouye, 1979), etc. Other promoters produced by recombinant DNA or synthetic techniques may also be used to provide for transcription of the inserted sequences.

Specific initiation signals are also required for efficient translation of inserted protein coding sequences. These signals include the ATG initiation codon and adjacent sequences. In cases where the native gene sequences encoding its own initiation codon and adjacent sequences are inserted into the appropriate expression vectors, no additional translational control signals may be needed. However, in cases where the native translational signals are not present, exogenous translational control signals, including the ATG initiation codon, must be provided. The initiation codon must furthermore be in phase with the reading frame of the protein coding sequences to ensure translation of the entire insert. These exogenous translational control signals and initiation codons can be of a variety of origins, both natural and synthetic.

Methods for constructing the appropriate expression vectors may include in vitro recombinant DNA and synthetic techniques and in vivo recombinations (genetic recombination). For reviews on maximizing gene expression, see Roberts and Lauer, 1979; Reznikoff and Gold, 1986.

U.S. Pat. No. 4,237,224 to Cohen and Boyer describes production of recombinant plasmids using processes of cleavage with restriction enzymes and joining with DNA ligase by known methods of ligation. These recombinant plasmids are then introduced by means of transformation and replicated in cellular cultures including prokaryotic organisms and eukaryotic cells grown in tissue culture.

Another method for introducing recombinant DNA molecules into unicellular organisms is described by Collins and Hohn in U.S. Pat. No. 4,304,863. This method utilizes a packaging/transduction system with bacteriophage vectors (cosmids).

The expression vector comprising the recombinant gene sequence should then be transferred into a bacterial host cell where it can replicate and be expressed or undergo conditional replication. This can be accomplished by any of numerous methods known in the art including but not limited to transformation (e.g., of isolated plasmid DNA into the attenuated bacterial host), phage transduction (Schmeiger, 1972), conjugation between bacterial host species, electroporation, etc.

In certain embodiments, a plasmid vector is contemplated for use to transform a host cell. In general, plasmid vectors containing replicon and control sequences which are derived from species compatible with the host cell are used in connection with these hosts. The vector ordinarily carries a replication site, as well as marking sequences which are capable of providing phenotypic selection in transformed cells. In a non-limiting example, E. coli is often transformed using derivatives of pBR322, a plasmid derived from an E. coli species. pBR322 contains genes for ampicillin and tetracycline resistance and thus provides easy means for identifying transformed cells. The pBR plasmid, or other microbial plasmid or phage must also contain, or be modified to contain, for example, promoters which can be used by the microbial organism for expression of its own proteins.

In addition, phage vectors containing replicon and control sequences that are compatible with the host microorganism can be used as transforming vectors in connection with these hosts. For example, the phage lambda GEM®-11 may be utilized in making a recombinant phage vector which can be used to transform host cells, such as, for example, E. coli LE392.

Further useful plasmid vectors include pIN vectors (Inouye et al., 1985); and pGEX vectors, for use in generating glutathione S-transferase (GST) soluble fusion proteins for later purification and separation or cleavage. Other suitable fusion proteins are those with β-galactosidase, ubiquitin, and the like.

Bacterial host cells, for example, E. coli, comprising the expression vector, are grown in any of a number of suitable media, for example, LB. The expression of the recombinant protein in certain vectors may be induced, as would be understood by those of skill in the art, by contacting a host cell with an agent specific for certain promoters, e.g., by adding IPTG to the media or by switching incubation to a higher temperature. After culturing the bacteria for a further period, generally of between 2 and 24 h, the cells are collected by centrifugation and washed to remove residual media.

a. Promoters and Enhancers

A "promoter" is a control sequence that is a region of a nucleic acid sequence at which initiation and rate of transcription are controlled. Transcription of DNA is dependent upon the presence of a promoter, which is a DNA sequence that directs the binding of RNA polymerase and thereby promotes mRNA synthesis. The DNA sequence of eukaryotic promoters differs from those of prokaryotic promoters. Furthermore, eukaryotic promoters and accompanying genetic signals may not be recognized in or may not function in a prokaryotic system, and furthermore, prokaryotic promoters are not recognized and do not function in eukaryotic cells. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30-110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the thymidine kinase promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the β-lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression, (see, for example Sambrook et al. 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

b. Initiation Signals and Internal Ribosome Binding Sites

A specific initiation signal also may be required for efficient translation of coding sequences. Translation of mRNA in prokaryotes depends upon the presence of the proper prokaryotic signals, which differ from those of eukaryotes. Efficient translation of mRNA in prokaryotes requires a ribosome binding site called the Shine-Dalgarno (S/D) sequence (Shine and Dalgarno, 1975) on the mRNA. This sequence is a short nucleotide sequence of mRNA that is located before the start codon, usually AUG, which encodes the amino-terminal (formyl-) methionine of the protein. The S/D sequences are complementary to the 3' end of the 16S rRNA (ribosomal RNA), and probably promote binding of mRNA to ribosomes by duplexing with the rRNA to allow correct positioning of the ribosome. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, each herein incorporated by reference).

c. Multiple Cloning Sites

Vectors can include a multiple cloning site (MCS), which is a nucleic acid region that contains multiple restriction enzyme sites, any of which can be used in conjunction with standard recombinant technology to digest the vector (see, for example, Carbonelli et al, 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

d. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

e. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

f. Selectable and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin, histidinol, and other antibiotic resistance genes are useful selectable markers. In addition to markers conferring a phenotype that allows for the discrimination of transformants based on the implementation of conditions, other types of markers including screenable markers such as GFP, whose basis is calorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

g. Plasmid Vectors

Regardless of the method used for construction, the recombinant DNA molecule must be compatible with the host cell, i.e., capable of autonomous replication in the host cell or stably integrated into one or more of the host cell's chromosomes or plasmids. The recombinant DNA molecule will typically have a marker function which allows the selection of the desired recombinant DNA molecule(s). In addition, if all of the proper replication, transcription, and translation signals are correctly arranged on the recombinant vector, the foreign gene will be properly expressed in, e.g., the transformed bacterial cells, in the case of bacterial expression plasmids.

2. Vector Delivery and Cell Transformation

Suitable methods for nucleic acid delivery for transformation of an organelle, a cell, a tissue or an organism for use with the current invention are believed to include virtually any method by which a nucleic acid (e.g., DNA) can be introduced into an organelle, a cell, a tissue or an organism, as described herein or as would be known to one of ordinary skill in the art. Such methods include, but are not limited to electroporation (U.S. Pat. No. 5,384,253, incorporated herein by reference; Tur-Kaspa et al., 1986; Potter et al., 1984); temperature shock, phage transfer and any combination of such methods. Through the application of techniques such as these cell(s) or organism(s) may be stably or transiently transformed/transfected.

a. Electroporation

In certain embodiments of the present invention, a nucleic acid is introduced into an organelle, a cell, a tissue or an organism via electroporation. Electroporation involves the exposure of a suspension of cells and DNA to a high-voltage electric discharge. In some variants of this method, certain cell wall-degrading enzymes, such as pectin-degrading enzymes, are employed to render the target recipient cells more susceptible to transformation by electroporation than untreated cells (U.S. Pat. No. 5,384,253, incorporated herein by reference). Alternatively, recipient cells can be made more susceptible to transformation by mechanical wounding.

Transfection of eukaryotic cells using electroporation has been quite successful. Mouse pre-B lymphocytes have been transfected with human kappa-immunoglobulin genes (Potter et al., 1984), and rat hepatocytes have been transfected with the chloramphenicol acetyltransferase (CAT) gene (Tur-Kaspa et al., 1986) in this manner.

b. Microprojectile Bombardment

Microprojectile bombardment techniques can be used to introduce a nucleic acid into at least one, organelle, cell, tissue or organism (U.S. Pat. No. 5,550,318; U.S. Pat. No. 5,538,880; U.S. Pat. No. 5,610,042; and PCT Application WO 94/09699; each of which is incorporated herein by reference). This method depends on the ability to accelerate DNA-coated microprojectiles to a high velocity allowing them to pierce cell membranes and enter cells without killing them (Klein et al., 1987). There are a wide variety of microprojectile bombardment techniques known in the art, many of which are applicable to the invention.

In this microprojectile bombardment, one or more particles may be coated with at least one nucleic acid and delivered into cells by a propelling force. Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold particles or beads. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. DNA-coated particles may increase the level of DNA delivery via particle bombardment but are not, in and of themselves, necessary.

For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into a cell (e.g., a plant cell) by acceleration is the Biolistics Particle Delivery System, which can be used to propel particles coated with DNA or cells through a screen, such as a stainless steel or Nytex screen, onto a filter surface covered with cells, such as for example, a monocot plant cells cultured in suspension. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large.

3. Host Cells

As used herein, the terms "cell," "strain," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic cell, and it includes any transformable organism that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny. As used herein, the terms "engineered" and "recombinant" cells or host cells are intended to refer to a cell into which an exogenous nucleic acid sequence, such as, for example, a vector, has been introduced. Therefore, recombinant cells are distinguishable from naturally occurring cells which do not contain a recombinantly introduced nucleic acid.

In certain embodiments, it is contemplated that RNAs or proteinaceous sequences may be co-expressed with other selected RNAs or proteinaceous sequences in the same host cell. Co-expression may be achieved by co-transfecting the host cell with two or more distinct recombinant vectors. Alternatively, a single recombinant vector may be constructed to include multiple distinct coding regions for RNAs, which could then be expressed in host cells transfected with the single vector.

In certain embodiments, the host cell may be comprised in at least one organism. In certain embodiments, the organism may be, but is not limited to, an animal, vertebrate, mammal, or human, as would be understood by one of ordinary skill in the art (see, for example, webpage at phylogeny.arizona.edu/tree/phylogeny.html).

Numerous cell lines and cultures are available for use as a host cell, and they can be obtained through the American Type Culture Collection (ATCC), which is an organization that serves as an archive for living cultures and genetic materials (www.atcc.org). An appropriate host can be determined by one of skill in the art based on the vector backbone and the desired result. A plasmid or cosmid, for example, can be introduced into a prokaryote host cell for replication of many vectors. Cell types available for vector replication and/or expression include, but are not limited to, bacteria, such as *E. coli* (e.g., *E. coli* strain RR1, *E. coli* LE392, *E. coli* B, *E. coli* X 1776 (ATCC No. 31537) as well as *E. coli* W3110 (F-, lambda-, prototrophic, ATCC No. 273325), DH5α, JM109, and KC8, bacilli such as *Bacillus subtilis*; and other Enterobacteriaceae such as *Salmonella typhimurium*, *Serratia marcescens*, various *Pseudomonas* species, as well as a number of commercially available bacterial hosts such as SURE® Competent Cells and SOLOPACK™ Gold Cells (STRATAGENE®, La Jolla). In certain embodiments, bacterial cells such as *E. coli* LE392 are particularly contemplated as host cells for phage viruses.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

4. Expression Systems

Numerous expression systems exist that comprise at least a part or all of the compositions discussed above. Prokaryote-based systems can be employed for use with the present invention to produce nucleic acid sequences, or their cognate polypeptides, proteins and peptides. Many such systems are commercially and widely available.

It is contemplated that the proteins, polypeptides or peptides produced by the methods of the invention may be "overexpressed", i.e., expressed in increased levels relative to its natural expression in cells. Such overexpression may be assessed by a variety of methods, including radio-labeling and/or protein purification. However, simple and direct methods are preferred, for example, those involving SDS/PAGE and protein staining or western blotting, followed by quantitative analyses, such as densitometric scanning of the resultant gel or blot. A specific increase in the level of the recombinant protein, polypeptide or peptide in comparison to the level in natural cells is indicative of overexpression, as is a relative abundance of the specific protein, polypeptides or peptides in relation to the other proteins produced by the host cell and, e.g., visible on a gel.

IV. Antigens

Heterologous antigens may be expressed in or by an attenuated bacterium of the present invention. As described herein, various antigens may be used in the context of bacteria lacking functional lpp vaccine vectors.

A. Pathogens

The present invention would have applications, therefore, in the prevention and treatment of diseases against which antigen-specific immune response would be effective. The following pathogenic virus classes, which are mentioned by way of example, are specifically contemplated as heterologous antigens: influenza A, B and C, parainfluenza, paramyxoviruses, Newcastle disease virus, respiratory syncytial virus, measles, mumps, parvoviruses, Epstein-Barr virus, rhinoviruses, coxsackieviruses, echoviruses, reoviruses, rhabdoviruses, lymphocytic choriomeningitis, coronavirus, polioviruses, herpes simplex, human immunodeficiency viruses, cytomegaloviruses, papillomaviruses, virus B, varicella-zoster, poxyiruses, rubella, rabies, picomaviruses, rotavirus and Kaposi associated herpes virus.

In addition to the viral diseases mentioned above, the present invention is also useful in the prevention, inhibition, or treatment of bacterial infections, including, but not limited to, the 83 or more distinct serotypes of pneumococci, streptococci such as *S. pyogenes, S. agalactiae, S. equi, S. canis, S. bovis, S. equinus, S. anginosus, S. sanguis, S. salivarius, S. mitis, S. mutans*, other viridans streptococci, peptostreptococci, other related species of streptococci, enterococci such as *Enterococcus faecalis, Enterococcus faecium*, staphylococci, such as *Staphylococcus epidermidis, Staphylococcus aureus, Hemophilus influenzae, Pseudomonas* species such as *Pseudomonas aeruginosa, Pseudomonas pseudomallei, Pseudomonas mallei*, brucellas such as *Brucella melitensis, Brucella suis, Brucella abortus, Bordetella pertussis, Borellia* species, such as *Borellia burgedorferi, Neisseria meningitidis, Neisseria gonorrhoeae, Moraxella catarrhalis, Corynebacterium diphtheriae, Corynebacterium ulcerans, Corynebacterium pseudotuberculosis, Corynebacterium pseudodiphtheriticum, Corynebacterium urealyticum, Corynebacterium hemolyticum, Corynebacterium equi*, etc. *Listeria monocytogenes, Nocordia asteroides, Bacteroides* species, Actinomycetes species, *Treponema pallidum, Leptospirosa* species, *Haemophilus* species, *Helicobacter* species, including *Helicobacter pylori, Treponema* species and related organisms. The invention may also be useful against gram-negative bacteria such as *Klebsiella pneumoniae, Escherichia coli, Proteus, Serratia* species, *Acinetobacter, Yersinia pestis, Francisella tularensis, Enterobacter* species, *Bacteriodes* and *Legionella* species, *Shigella* species, *Mycobacterium* species (e.g., *Mycobacterium tuberculosis, Mycobacterium bovis* or other mycobacteria infections), *Mycobacterium avium* complex (MAC), *Mycobacterium marinum, Mycobacterium fortuitum, Mycobacterium kansaii, Yersinia* infections (e.g., *Yersinia pestis, Yersinia enterocolitica* or *Yersinia pseudotuberculosis*) and the like. In addition, the invention in contemplated to be of use in controlling protozoan, helminth or other macroscopic infections by organisms such as *Cryptosporidium, Entamoeba, Plasmodiium, Giardia, Leishmania, Trypanasoma, Trichomonas, Naegleria, Isospora belli, Toxoplasma gondii, Trichomonas vaginalis, Wunchereria, Ascaris, Schistosoma* species, *Cyclospora* species, for example, and for *Chlamydia trachomatis* and other *Chlamydia* infections such as *Chlamydia psittaci*, or *Chlamydia pneumoniae*, for example. Of course it is understood that the invention may be used on any pathogen against which an effective antibody can be made.

Fungal and other mycotic pathogens (some of which are described in Human Mycoses, E. S. Beneke, Upjohn Co.: Kalamazoo, Mich., 1979; Opportunistic Mycoses of Man and Other Animals, J. M. B. Smith, CAB International: Wallingford, UK, 1989; and Scrip's Antifungal Report, by PJB Publications Ltd, 1992) are also contemplated as a target of administration of an attenuated bacterial vaccine vector. Fungi disease contemplated in the context of the invention include, but are not limited to, Aspergillosis, Black piedra, Candidiasis, Chromomycosis, Cryptococcosis, Onychomycosis, or *Otitis externa* (otomycosis), Phaeohyphomycosis, Phycomycosis, *Pityriasis versicolor*, ringworm, *Tinea barbae, Tinea capitis, Tinea corporis, Tinea cruris, Tinea favosa, Tinea imbricata, Tinea manuum, Tinea nigra* (palmaris), *Tinea pedis, Tinea unguium*, Torulopsosis, *Trichomycosis axillaris, White piedra*, and their synonyms, to severe systemic or opportunistic infections, such as, but not limited to, Actinomycosis, Aspergillosis, Candidiasis, Chromomycosis, Coccidioidomycosis, Cryptococcosis, Entomophthoramycosis, Geotrichosis, Histoplasmosis, Mucormycosis, Mycetoma, Nocardiosis, North American Blastomycosis, Paracoccidioidomycosis, Phaeohyphomycosis, Phycomycosis, Pneumocystic pneumonia, Pythiosis, Sporotrichosis, and Torulopsosis, and their synonyms, some of which may be fatal. Known fungal and mycotic pathogens include, but are not limited to, *Absidia* spp., *Actinomadura madurae*, *Actinomyces* spp., *Allescheria boydii*, *Alternaria* spp., *Anthopsis deltoidea*, *Apophysomyces elegans*, *Arnium leoporinum*, *Aspergillus* spp., *Aureobasidium pullulans*, *Basidiobolus ranarum*, *Bipolaris* spp., *Blastomyces dermatitidis*, *Candida* spp., *Cephalosporium* spp., *Chaetoconidium* spp., *Chaetomium* spp., *Cladosporium* spp., *Coccidioides immitis*, *Conidiobolus* spp., *Corynebacterium tenuis*, *Cryptococcus* spp., *Cunninghamella bertholletiae*, *Curvularia* spp., *Dactylaria* spp., *Epidermophyton* spp., *Epidermophyton floccosum*, *Exserophilum* spp., *Exophiala* spp., *Fonsecaea* spp., *Fusarium* spp., *Geotrichum* spp., *Helminthosporium* spp., *Histoplasma* spp., *Lecythophora* spp., *Madurella* spp., *Malassezia furfur*, *Microsporum* spp., *Mucor* spp., *Mycocentrospora acerina*, *Nocardia* spp., *Paracoccidioides brasiliensis*, *Penicillium* spp., *Phaeosclera dematioides*, *Phaeoannellomyces* spp., *Phialemonium obovatum*, *Phialophora* spp., *Phoma* spp., *Piedraia hortai*, *Pneumocystis carinii*, *Pythium insidiosum*, *Rhinocladiella aquaspersa*, *Rhizomucor pusillus*, *Rhizopus* spp., *Saksenaea vasiformis*, *Sarcinomyces phaeomuriformis*, *Sporothrix schenckii*, *Syncephalastrum racemosum*, *Taeniolella boppii*, *Torulopsosis* spp., *Trichophyton* spp., *Trichosporon* spp., *Ulocladium chartarum*, *Wangiella dermatitidis*, *Xylohypha* spp., *Zygomyetes* spp. and their synonyms. Other fungi that have pathogenic potential include, but are not limited to, *Thermomucor indicae-seudaticae*, *Radiomyces* spp., and other species of known pathogenic genera.

B. Tumor Antigens

In addition, it is specifically contemplated that antigenic epitopes derived from tumor antigens may be employed in the context of the invention. Known tumor antigens include, but are not limited to: Adenocorticotropic Hormone (ACTH), Aldosterone, Alphafetoprotein (AFP), Beta-2-Microglobulin (B2M), CA 15-3TM, CA 125TM, CA 19-9TM, CA 19-9TM, CA 549TM, Carcinoembryonic Antigen (CEA), p53, Rb, MelanA, HER2/neu, gp100, Ferritin, Gastrin, human Chorionic Gonadotropin (hCG), beta hCG, Gamma Enolase (NSE), Prolactin, Prostatic Acid Phosphatase (PAP), Multiple Melanoma Antigens (MMAs), Prostate Specific Antigen (PSA), Tissue Polypeptide Antigen (TPA), Calcitonin, HOJ-1, estrogen receptor, laminin receptor, erb B, Sialyl Lewis Antigens, tyrosinase, ras, HMFG, -2 and -3, and LD-1.

C. Self-Antigens

In addition to the diseases mentioned above, the present invention is also useful in the prevention, inhibition, or treatment of autoimmune diseases. In this invention, it is specifically contemplated that antigenic epitopes derived from body self-proteins may be employed in the context of the invention. Known self antigens include, but are not limited to: GAD (glutamic acid decarboxylase), MBP (myelin base protein), Ku protein, thyroglobulin, insulin, acetocholine receptor, snRNP, corticotropin, ATPase proton pump.

In alternative embodiments fusion proteins comprising an antigen of interest may be expressed on the bacterial cell surface or secreted from the bacteria. An antigen need not be expressed by an attenuated bacteria of the invention. An antigen may be covalently coupled to the surface of an attenuated bacteria.

V. Pharmaceutical Preparations

Pharmaceutical compositions of the present invention comprise an effective amount of one or more attenuated bacterium of the Enterobacteriaceae family with a mutant or altered lipoprotein or additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of an pharmaceutical composition that contains at least one attenuated bacterium of the Enterobacteriaceae family with a mutant lipoprotein or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The attenuated bacterium of the invention may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine.

The present invention contemplates vaccines for use in both active and passive immunization, in certain embodiments. Immunogenic compositions, proposed to be suitable for use as a vaccine, may be prepared most readily directly from attenuated bacteria of the Enterobacteriaceae family, prepared in a manner disclosed herein. In various embodiments, an antigenic material may be extensively dialyzed to remove undesired small molecular weight molecules and/or lyophilized for more ready formulation into a desired vehicle.

Typically, vaccines are prepared as injectables. Either as liquid solutions or suspensions: solid forms suitable for solution in, or suspension in, liquid prior to injection may also be prepared. The preparation may also be emulsified. In embodiments where the composition is in a liquid form, a carrier can be a solvent or dispersion medium comprising but not limited to, water, ethanol, polyol (e.g., glycerol, propylene glycol, liquid polyethylene glycol, etc), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof. In addition, if desired, the vaccine may contain minor amounts of auxiliary substances such as wetting or emulsifying agents, pH buffering agents, or adjuvants which enhance the effectiveness of the vaccines. Additionally, iscom, a supramolecular spherical structure, may be used for parenteral and mucosal vaccination (Morein et al., 1998).

Sterile injectable solutions may be prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

Various methods of achieving adjuvant effect for the vaccine includes use of agents such as aluminum hydroxide or phosphate (alum), commonly used as about 0.05 to about 0.1% solution in phosphate buffered saline, admixture with synthetic polymers of sugars (Carbopol®) used as an about 0.25% solution, aggregation of the protein in the vaccine by heat treatment with temperatures ranging between about 70° to about 101° C. for a 30-second to 2-minute period, respectively. Aggregation by reactivating with pepsin treated (Fab) antibodies to albumin, mixture with bacterial cells such as *C. parvum* or endotoxins or lipopolysaccharide components of gram-negative bacteria, emulsion in physiologically acceptable oil vehicles such as mannide mono-oleate (Aracel A) or emulsion with a 20% solution of a perfluorocarbon (Fluosol-DA®) used as a block substitute may also be employed.

Adjuvants that may be used in the practice of the invention include, but are not limited to Adjumer™, Adju-Phos®, Algal Glucan, Algammulin, Alhydrogel, Antigen Formulation, Avridine®, BAY R1005, Calcitriol, Calcium Phosphate Gel, Cholera holotoxin (CT), Cholera toxin B subunit (CTB), Cholera toxin A1-subunit-Protein A D-fragment fusion protein, CRL1005, Cytokine-containing Liposome, Dimethyldioctadecylammonium bromide, Dehydroepiandrosterone; Dimyristoyl phosphatidyl choline; 1,2-dimyristoyl-sn-3-phosphatidylcholine, Dimyristoyl phosphatidylglycerol, Deoxycholic Acid Sodium Salt; Freund's Complete Adjuvant, Freund's Incomplete Adjuvant, Gamma Inulin, Gerbu Adjuvant®, GM-C SF, N-acetylglucosaminyl-($\beta$1-4)-N-acetylmuramyl-L-alanyl-D-isoglutamine, Imiquimod, ImmTher™, Interferon-$\gamma$, Interleukin-1$\beta$, Interleukin-2, Interleukin-7, Interleukin-12, ISCOM™, Iscoprep 7.0.3.™, Liposome, Loxoribine, LT-OA or LT Oral Adjuvant, MF59, MONTANIDE ISA 51, MONTANIDE ISA 720, MPLTM, MTP-PE, MTP-PE Liposome, Murametide, Murapalmitine, D-Murapalmitine, NAGO, Non-Ionic Surfactant Vesicle, Pleuran, lactic acid polymer, glycolic acid polymer, Pluronic® L121, Polymethyl methacrylate, PODDS™, Poly rA:Poly rU, Polysorbate 80, Protein Cochleate, QS-21, Quil-A, Rehydragel™ HPA, Rehydragel™ LV, S-28463, SAF-1, Sclavo peptide, Sendai Proteoliposome, Sendai-containing Lipid Matrix, Span 85, Specol, Squalane, Squalene, Stearyl Tyrosine, Theramide™, Threonyl-MDP, Ty Particle, or Walter Reed Liposome.

Any of the conventional methods for administration of a vaccine are applicable. These include, but are not limited to oral application on a solid physiologically acceptable base or in a physiologically acceptable dispersion, parenterally, by injection or the like. Vaccines of the invention may be administered parenterally, by injection, for example, either subcutaneously or intramuscularly. Additional formulations which are suitable for other modes of administration include suppositories and, in some cases, oral formulations. In other embodiments, one may use eye drops, nasal solutions or sprays, aerosols or inhalants in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in preferred embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

In certain embodiments, the attenuated bacterium of the invention is prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain preferred embodiments, an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both. Oral formulations may contain about 10 to about 95% of active ingredient, preferably about 25 to about 70%.

Additional formulations which are suitable for other modes of administration include suppositories. Suppositories are solid dosage forms of various weights and shapes, usually medicated, for insertion into the rectum, vagina or urethra. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%. The dosage of the vaccine will depend on the route of administration and will vary according to the size of the host.

In certain embodiments, vaccines may comprise, for example, at least about 0.1% of an active compound. In other embodiments, an active compound may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more of antigen or total protein per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

The vaccines are administered in a manner compatible with the dosage formulation, and in such amount as will be therapeutically effective and immunogenic. The quantity to be administered depends on the subject to be treated, including, e.g., the capacity of the individual's immune system to synthesize antibodies, and the degree of protection desired. Precise amounts of active ingredient required to be administered depend on the judgment of the practitioner. However, suitable dosage ranges are of the order of several hundred micrograms active ingredient per vaccination. Suitable regimes for initial administration and booster shots are also variable, but are typified by an initial administration followed by subsequent inoculations or other administrations.

In many instances, it will be desirable to have multiple administrations of the vaccine, usually not exceeding six vaccinations, more usually not exceeding four vaccinations and preferably one or more, usually at least about three vaccinations. The vaccinations will normally be at from two to twelve week intervals, more usually from three to five week intervals. Periodic boosters at intervals of 1-5 years, usually three years, will be desirable to maintain protective levels of the antibodies. The course of the immunization may be followed by assays for antibodies for the supernatant antigens. The assays may be performed by labeling with conventional labels, such as radionuclides, enzymes, fluorescents, and the like. These techniques are well known and may be found in a wide variety of patents, such as U.S. Pat. Nos. 3,791,932; 4,174,384 and 3,949,064, as illustrative of these types of assays.

"Unit dose" is defined as a discrete amount of a therapeutic composition dispersed in a suitable carrier. For example, in accordance with the present methods, bacterial doses include a particular number of bacteria or colony forming units (cfu). For embodiments involving bacteria, particular unit doses include $10^3$, $10^4$, $10^5$, $10^6$, $10^7$, $10^8$, $10^9$, $10^{10}$, $10^{11}$, $10^{12}$, $10^{13}$, $10^{14}$ or $10^{15}$ cfu or bacteria particles.

In this connection, sterile aqueous media which can be employed will be known to those of skill in the art in light of the present disclosure. For example, a unit dose could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

VI. Kits

Any of the compositions described herein may be comprised in a kit. In a non-limiting example, an attenuated bacterium of the Enterobacteriaceae family with a non-functional lipoprotein and/or additional agent, may be comprised in a kit. The kits will thus comprise, in suitable container means, a attenuated bacterium of the Enterobacteriaceae family with a non-functional lipoprotein and/or an additional agent of the present invention.

The kits may comprise a suitably aliquoted attenuated bacterium of the Enterobacteriaceae family with a non-functional lipoprotein and/or additional agent compositions of the present invention, whether labeled or unlabeled, as may be used to prepare a standard curve for a detection assay. The components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing the attenuated bacterium of the Enterobacteriaceae family with a non-functional lipoprotein, additional agent, and any other reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being particularly preferred. The attenuated bacterium of the Enterobacteriaceae family with a non-functional lipoprotein compositions may also be formulated into a syringeable composition. In which case, the container means may itself be a syringe, pipette, and/or other such like apparatus, from which the formulation may be applied to an infected area of the body, injected into an animal, and/or even applied to and/or mixed with the other components of the kit.

However, the components of the kit may be provided as dried powder(s). When reagents and/or components are provided as a dry powder, the powder can be reconstituted by the addition of a suitable solvent. It is envisioned that the solvent may also be provided in another container means.

The container means will generally include at least one vial, test tube, flask, bottle, syringe and/or other container means, into which the attenuated bacterium of the Enterobacteriaceae family with a non-functional lipoprotein and/or antigenic formulation are placed, preferably, suitably allocated. The kits may also comprise a second container means for containing a sterile, pharmaceutically acceptable buffer and/or other diluent.

The kits of the present invention will also typically include a means for containing the vials in close confinement for commercial sale, such as, e.g., injection and/or blow-molded plastic containers into which the desired vials are retained.

Irrespective of the number and/or type of containers, the kits of the invention may also comprise, and/or be packaged with, an instrument for assisting with the injection/administration and/or placement of the ultimate attenuated bacterium of the Enterobacteriaceae family with a non-functional lipoprotein composition within the body of an animal. Such an instrument may be a syringe, pipette, forceps, and/or any such medically approved delivery vehicle.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Generation of lpp Gene Deficient Mutant of *Salmonella Typhimurium* TML

Based on the genomic sequence of Salmonella species available from the Sanger Centre (Genome Research Center, UK) and the Institute for Biomedical Computing, Washington University, St. Louis, it was discovered that there were two copies of the lipoprotein gene (lpp) on the Salmonella chromosome separated by 82 bp. While the lpp1 gene had 237 bp, the lpp2 gene of Salmonella contained 240 bp. The DNA and amino acid sequence homologies between the two copies of the lipoprotein were 79% and 86%, respectively (FIG. 8 and FIG. 9). Significant homologies between the two copies of Salmonella and *E. coli* LP were also noted, as depicted in FIG. 8 and FIG. 9. Although the location of the lpp gene on Salmonella chromosome is not yet known, the structural gene for LP in *E. coli* has been mapped at 36 min. In order to understand the role of the lpp gene in the pathogenesis of Salmonella infections, the lpp gene isogenic mutant was constructed via double-crossover, homologous recombination. In this mutant, both the copies of the lpp gene were removed and replaced with a kanamycin resistance gene cassette. In certain embodiments of the invention additional genes encoding an antigen may also be inserted along with a selective marker, such as a kanamycin resistance gene. The strategy used to construct the lpp gene knockout strain of *S. typhimurium* TML is summarized in FIG. 1.

Briefly, the chromosomal DNA was isolated from a virulent strain *S. typhimurium* TML using standard techniques and subjected to polymerase chain reaction (PCR) analysis. The specific primers BamHI-F1 and XhoI-R2 were used to obtain a 1.6-kb 5'-flanking sequence to the lpp genes (FIG. 1). An exemplary program for PCR includes denaturation (94° C., 2 min), followed by 30 cycles of 94° C., 1 min and 68° C., 3 min. The final extension is performed at 72° C. for 7 min. The PCR products were isolated from the agarose gel, purified, and subjected to automated DNA sequence analysis to verify the identity of the PCR products. The selected primers were commercially synthesized, and the sequences of the primers used were as follows, with underlined bases representing the restriction sites engineered within the primers:

```
                                       (SEQ ID NO. 9)
BamHI-F1-   5-GTGGATCCTATGCAGAACACGGTCAGCG-3' and (SEQ ID NO. 10)
XhoI-R2     5-AGCTCGAGCTAGATTGAGTTAATCTTCCA-3'.
```

Likewise, primers XhoI-F2 (5-AT CTCGAGTACTGCGAAGGCTACTGCGTCC-3' (SEQ ID NO. 11)) and ApaI-R1 (5-AA GGGCCCTTCGCTGGCGATGTATAAC-3' (SEQ ID NO. 12)) were used to amplify a 1.7-kb 3' flanking sequence to the lpp genes (FIG. 1). These flanking sequences were needed for the homologous recombination to occur. Subsequently, the plasmid vector pBluescript was digested with the restriction enzymes BamHI and XhoI and the 5' flanking sequence to the lpp genes represented by the 1.6-kb BamHI-XhoI fragment was ligated into this vector and transformed into an *E. coli* DH5α strain to generate a 4.5-kb pBluelp recombinant plasmid (FIG. 1). The isolated 4.5-kb pBluelp plasmid was digested with XhoI and ApaI restriction enzymes and the 3' flanking sequence to the lpp genes represented by the 1.7-kb XhoI-ApaI fragment was then ligated into the above mentioned plasmid to generate a 6.2-kb recombinant plasmid pBluelp as shown in FIG. 1.

A 1.4-kb kanamycin-resistance gene cassette from plasmid pUC4K was inserted in place of the lpp genes at the XhoI restriction site of a 6.2-kb pBluelp plasmid to generate a 7.6-kb pBluelpK recombinant plasmid. Subsequently, a 4.7-kb BamHI and ApaI DNA fragment from this plasmid was isolated and ligated at the compatible restriction sites of a suicide vector pJQ200SK to generate a 10.0-kb pJQ2001pK plasmid (FIG. 1). The suicide vector pJQ200 contains a P15A origin of replication, a levan sucrase gene (sacB) from *Bacillus subtilis*, and a gentamicin-resistance gene. The sacB gene may be induced with 5% sucrose, resulting in cell killing as a result of SacB over-production. Therefore, while the single crossover mutants will be sensitive to sucrose and resistant to gentamicin, the genuine double crossover mutants will acquire sucrose-resistant and gentamicin-sensitive phenotype as a result of the loss of suicide vector from the host chromosome. The pJQ2001pK plasmid was maintained in a *E. coli* S17-1 strain, which contained a λpir gene integrated into its chromosome. The λpir gene provided π protein in trans for replication of the suicide vector only in *E. coli* S 17-1.

The *E. coli* S17-1 strain with the pJQ2001pK plasmid was conjugated with a wild-type spontaneous nalidixic acid resistant *S. typhimurium* TML. The resulting transconjugants, which are resistant to nalidixic acid, kanamycin and sucrose were picked up and further analyzed to confirm double crossover homologous recombination by PCR and Southern blot analyses. The suicide vector was unable to replicate in Salmonella as the later lacked π protein. Both the wild type and the lpp gene knockout strains of *S. typhimurium* were then examined in a mouse model of infection and in different in vitro assays.

Example 2

In Vivo Assays

Figure 2:
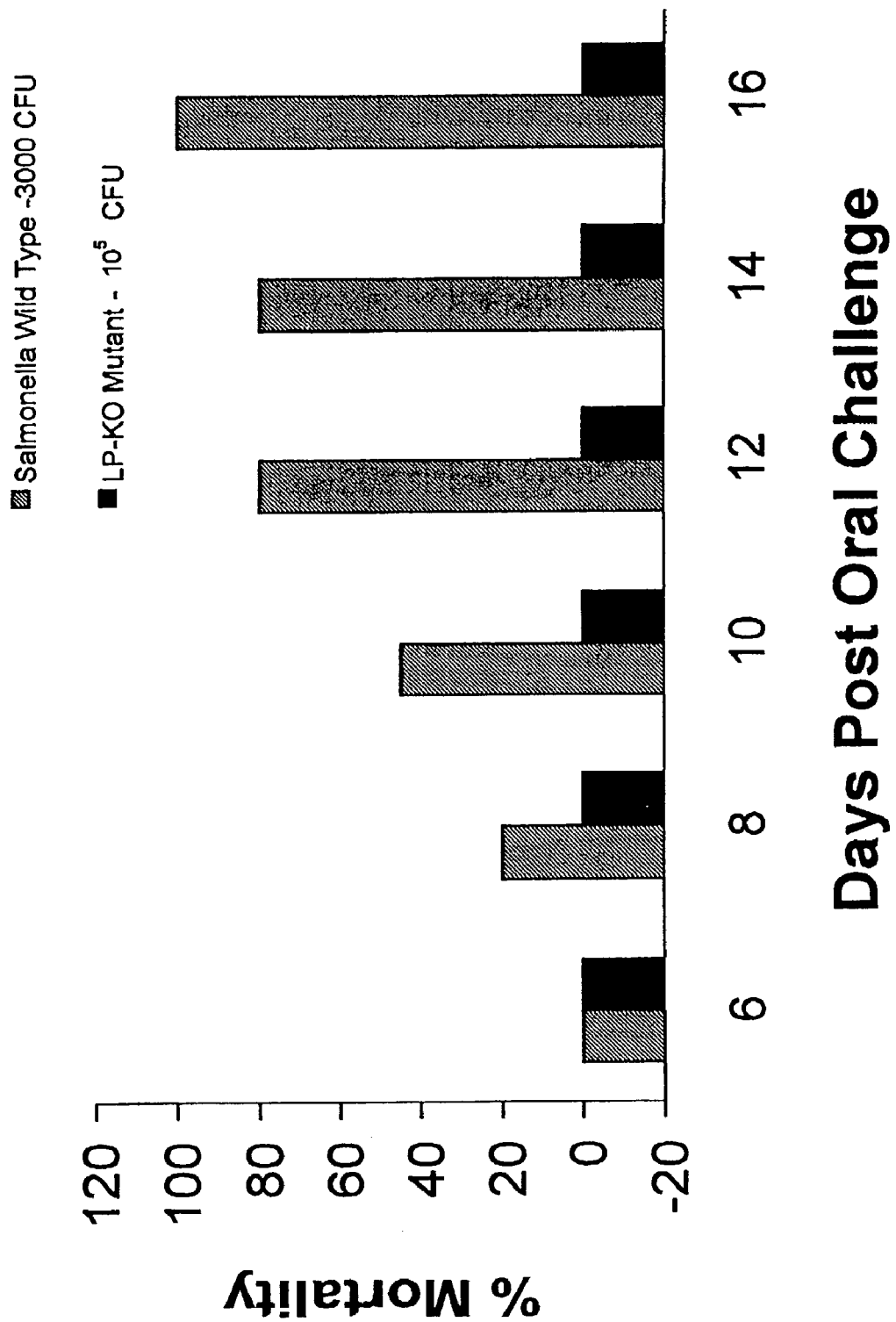
FIG. 2 illustrates an exemplary study of mortality after oral challenge. Mice (C57/B16-females) were challenged with varying numbers of either wild type *S. typhimurium* or a LP knockout mutant of *S. typhimurium*. Mice were challenged with varying doses (colony forming units, CFU) of these bacteria via an oral route of challenge. Mice were followed for two months for mortality.
Figure 3:
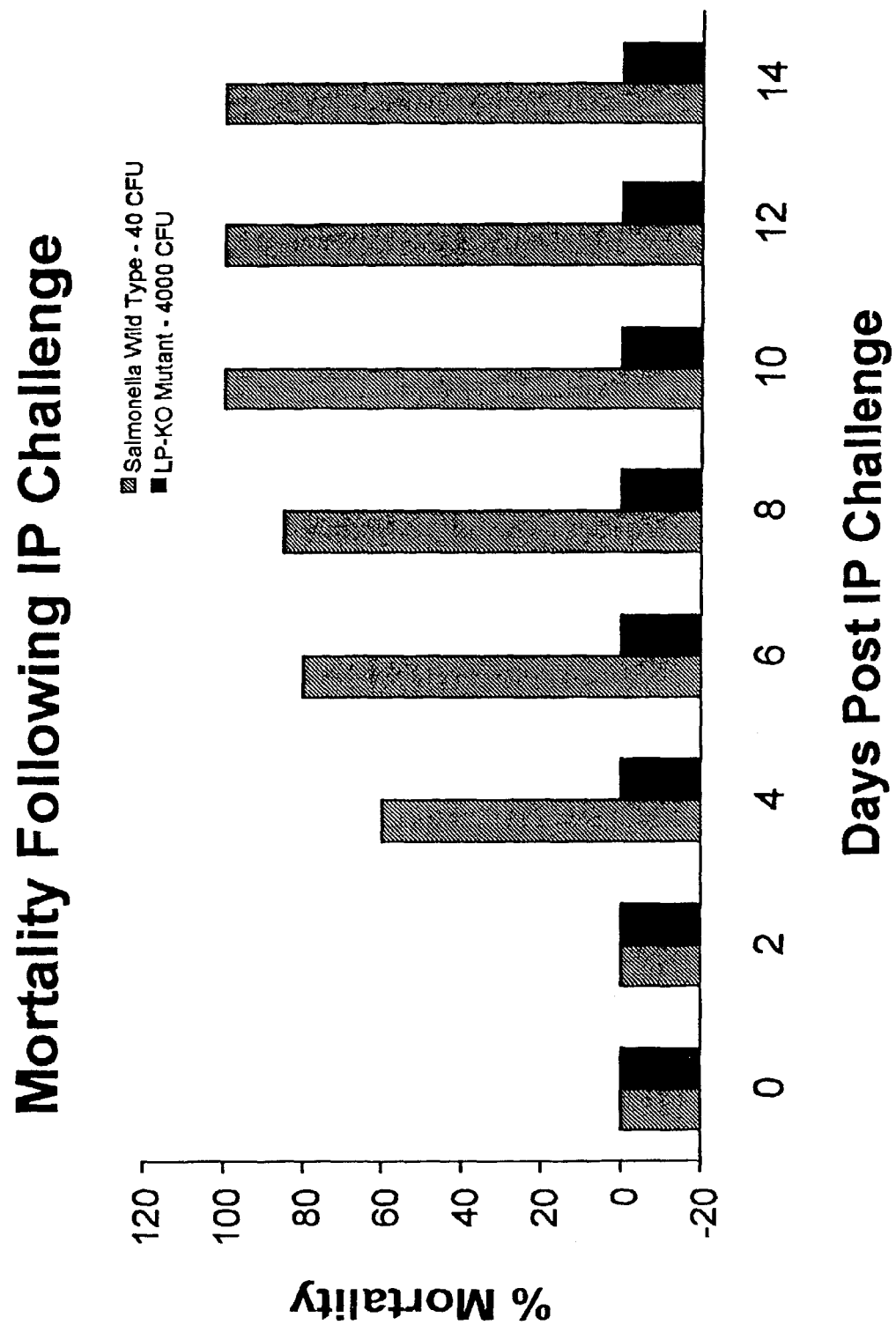
FIG. 3 illustrates an exemplary study of mortality after IP challenge. Mice (C57/B16-females) were challenged with varying numbers of either wild type *S. typhimurium* or a LP knockout mutant of *S. typhimurium*. Mice were challenged with varying doses (colony forming units, CFU) of these bacteria via an intraperitoneal (IP) route of challenge. Mice were followed for two months for mortality.
Figure 4:
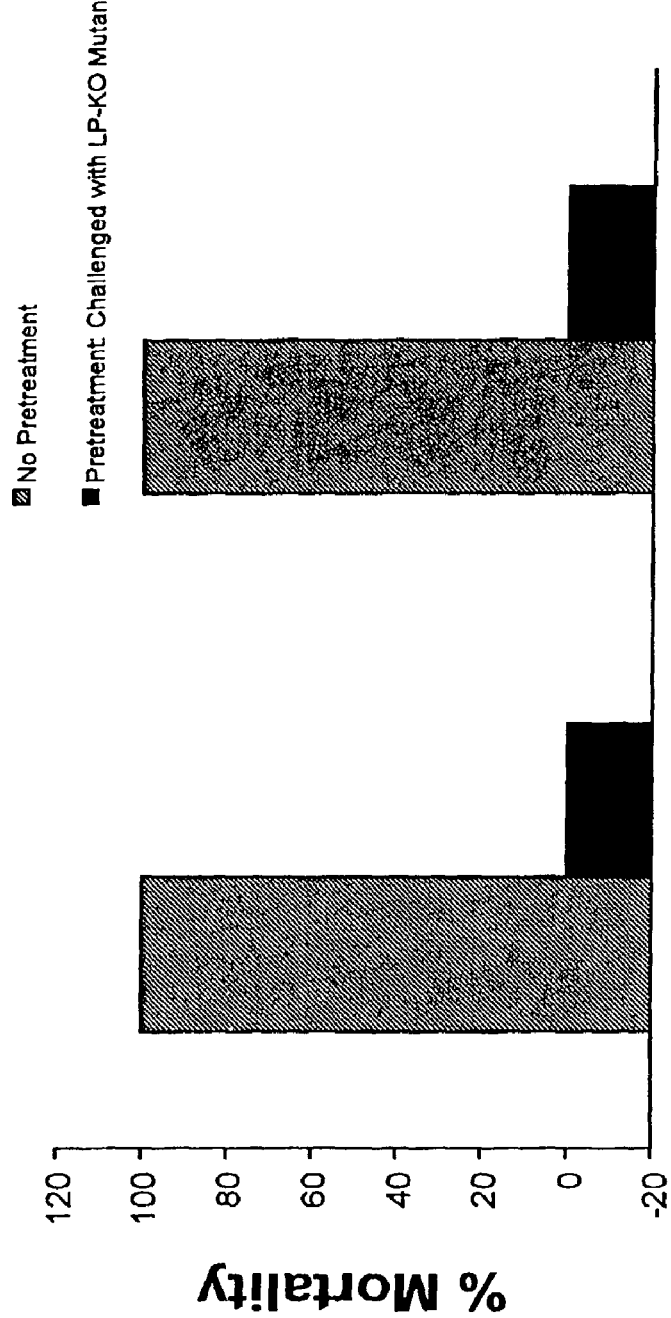
FIG. 4 illustrates an exemplary study of the immunogenicity of bacteria 12 days post *Salmonella* challenge. Mice were challenged with a knockout lpp mutant *Salmonella* either orally or IP and then rested for one month. Control mice were challenged with saline. These mice were then challenged with wild type *Salmonella* either orally or IP and monitored for survival and disease.

To investigate whether the LP deletion mutant of *Salmonella typhimurium* had altered virulence properties, a well-established mouse model was used. In initial studies, mice (C57/B16-females) were challenged with varying numbers of either wild type *S. typhimurium* or the LP deletion mutant of Salmonella. Mice were challenged with varying doses (colony forming units, CFU) of these bacteria via oral or intraperitoneal (IP) routes of challenge. Mice were followed for two months for mortality. Results of a representative study are presented in FIG. 2 and FIG. 3. LP deficient Salmonella had no adverse health effects on mice following either oral challenge or via IP challenge. Mice observed after two months following challenge looked exactly identical to control, un-challenged, mice. In contrast, mice challenged with wild type Salmonella died at day 10 to day 12 following oral or IP challenge. A lethal dose of Salmonella for oral challenge was 3000 CFU and for IP challenge 40 CFU. Mice challenged with two logs higher numbers of LP deficient Salmonella were healthy and showed no signs of disease or discomfort (FIG. 2). To investigate whether the LP deficient mutant Salmonella might immunize mice to Salmonella, a series of studies were performed. Mice were challenged with LP deficient mutant Salmonella either orally (3,000 CFU) or IP (3,000 CFU) and then rested for one month. Control mice were challenged with saline. These mice were then challenged with wild type Salmonella either orally (3000 CFU) or IP (40 CFU) and monitored for survival and disease. Mice immunized with LP deficient Salmonella were completely protected from wild type Salmonella challenge (FIG. 4). These mice showed no signs of disease and no deaths occurred over a two month period of observation.

Example 3

In Vitro Assays for Virulence

Figure 5:
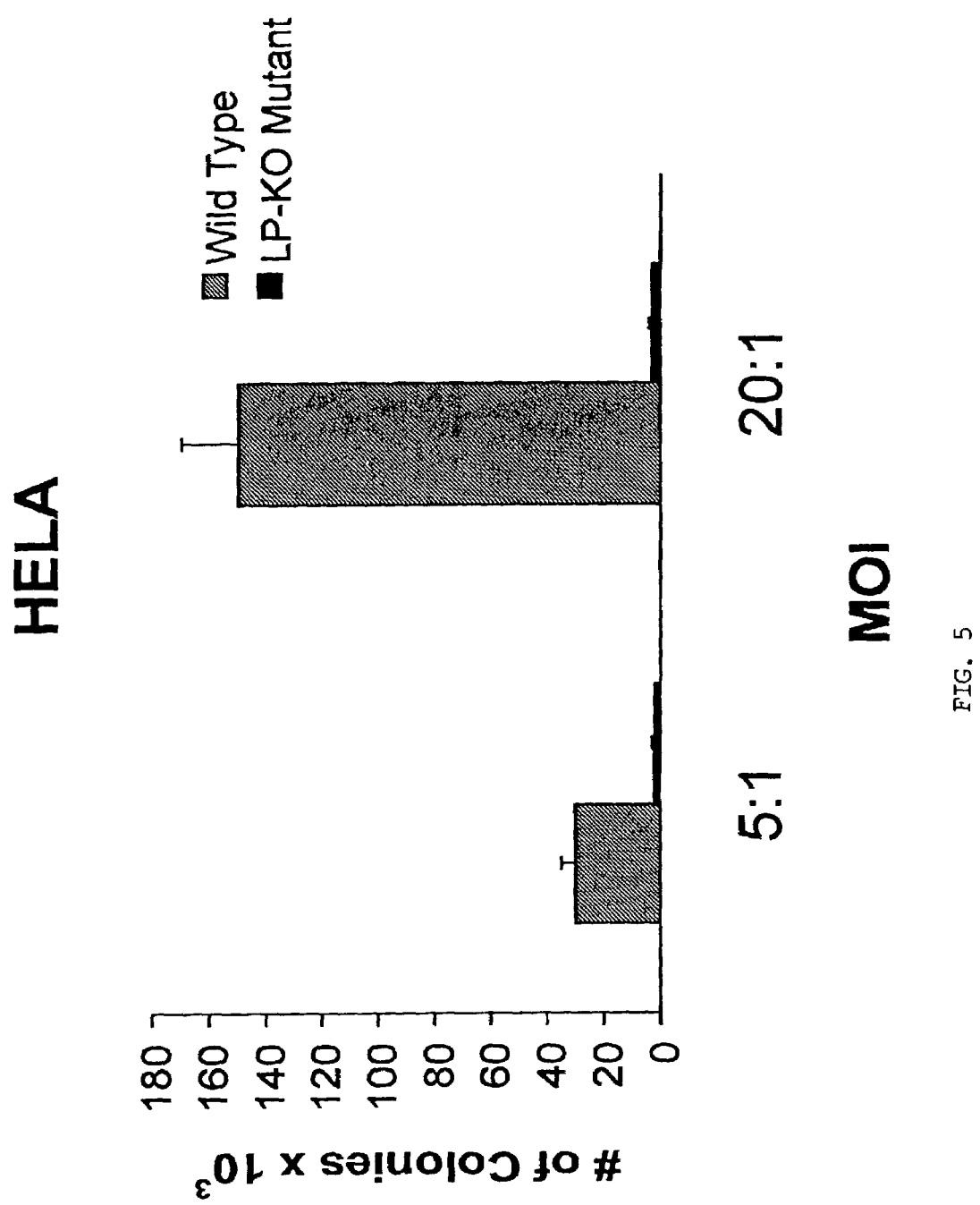
FIG. 5 illustrates an exemplary in vitro HeLa cell virulence assay. A series of studies were performed to assess whether or not these bacteria could invade cells and/or induce cytokine production. For these experiments, a well-established bacterial invasion model using human HeLa cells were used.
Figure 6:
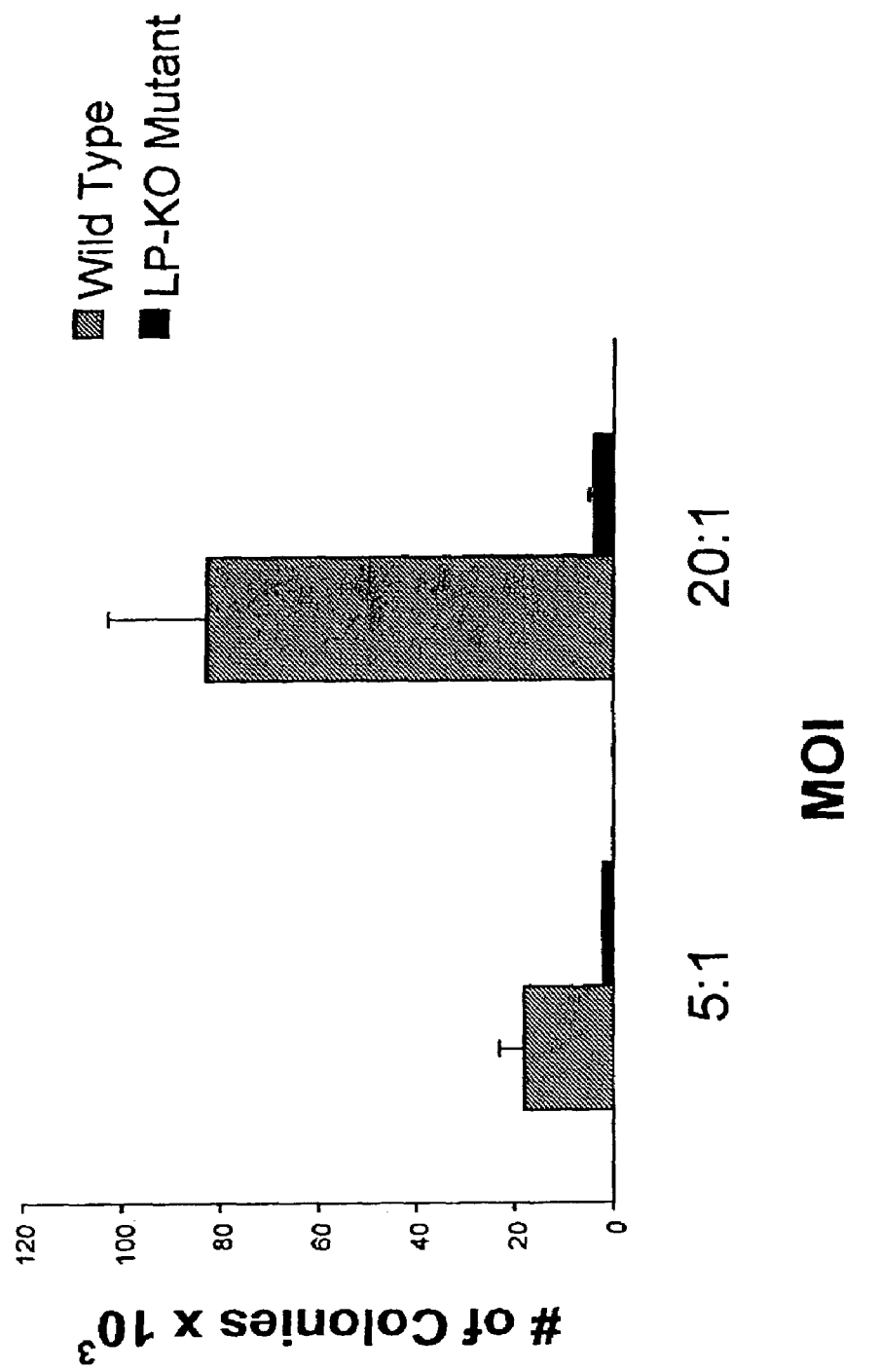
FIG. 6 illustrates an exemplary in vitro T84 cell virulence assay. A series of studies were performed to assess whether or not these bacteria could invade cells and/or induce cytokine production. For these experiments, a well-established bacterial invasion model using a human intestinal epithelial cell line, T84 were used.
Figure 7:
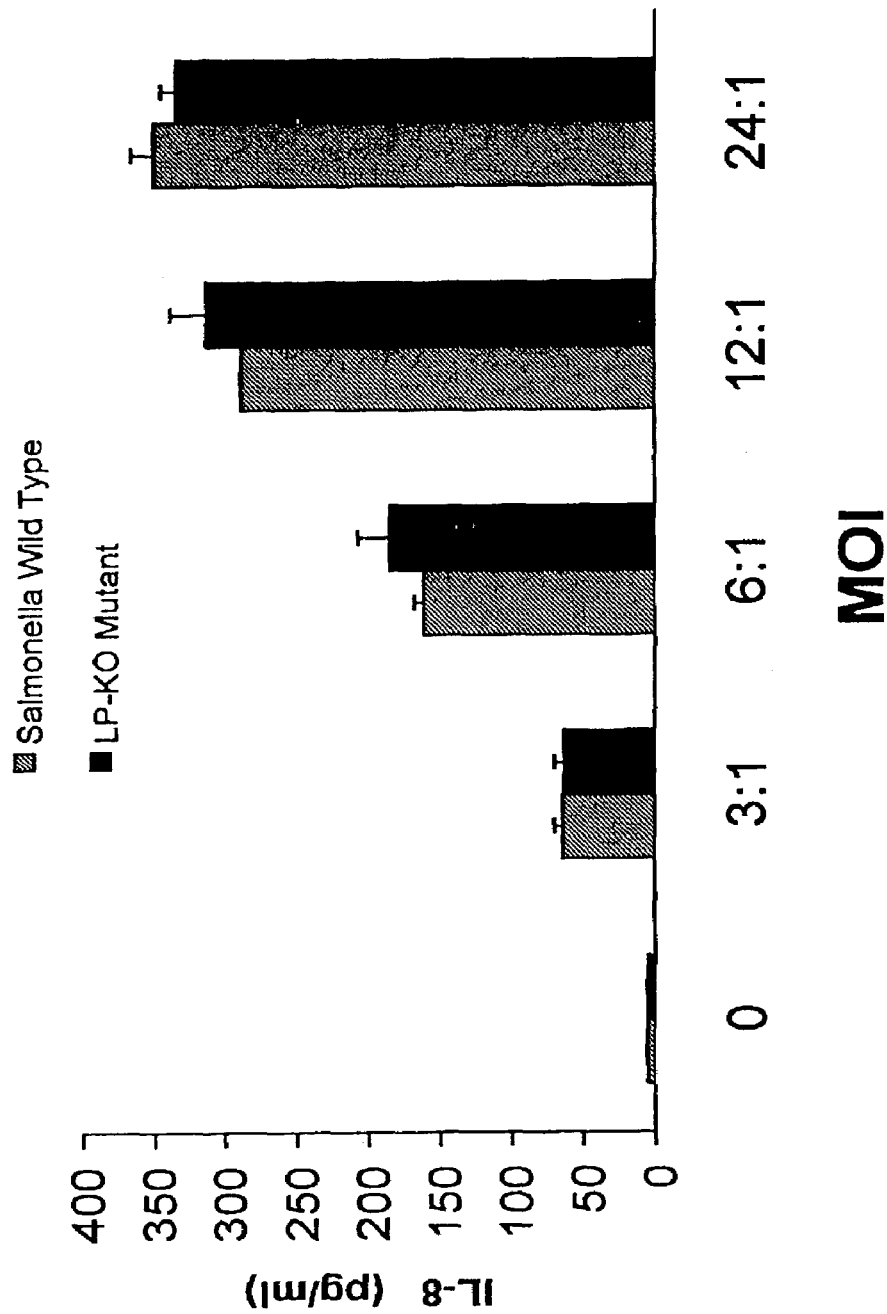
FIG. 7 illustrates the results of an exemplary IL-8 production assay in T84 cells.

To further investigate the LP deletion mutant of Salmonella, a series of studies were performed to assess whether or not these bacteria could invade cells and/or induce cytokine production. For these experiments, a well-established bacterial invasion model using human HeLa cells or a human intestinal epithelial cell line, T84 were used. As seen in FIG. 5 and FIG. 6, the LP deletion mutant Salmonella was significantly altered in its ability to invade either of these cell types. However, wild type Salmonella and the LP deletion mutant of Salmonella both bound equally well to the cell surface of these cells. In addition, the mutant Salmonella was not defective in replication once inside the host cells. In this regard, the LP deletion mutant of Salmonella induced IL8 production following interaction with T84 cells and the levels of IL8 induced by the LP deletion mutant of *Salmonella* was no different from that induced by the wild type *Salmonella* (FIG. 7). Thus, the LP deletion mutant of *Salmonella* differs significantly from the wild type for cellular invasion and for in vivo virulence. The ability to bind to the surface of a cell appears to be intact in the LP deficient mutant of *Salmonella* and there is no difference between the LP deletion mutant of *Salmonella* versus wild type *Salmonella* with regards to inducing IL8 production. These properties (ability to attach to a cell and to induce IL8 production) may be important characteristics associated with how the LP deletion mutant *Salmonella* may induce an adaptive immune response that offers protection from subsequent challenge with wild type *Salmonella*.

All of the COMPOSITIONS and/or METHODS disclosed and claimed herein can be made and executed without undue experimentation in light of the present disclosure. While the compositions and methods of this invention have been described in terms of preferred embodiments, it will be apparent to those of skill in the art that variations may be applied to the COMPOSITIONS and/or METHODS and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,550,081
U.S. Pat. No. 4,735,801
U.S. Pat. No. 4,837,151
U.S. Pat. No. 5,705,629
U.S. Pat. No. 4,659,774
U.S. Pat. No. 4,816,571
U.S. Pat. No. 5,141,813
U.S. Pat. No. 5,264,566
U.S. Pat. No. 4,959,463
U.S. Pat. No. 5,428,148
U.S. Pat. No. 5,554,744
U.S. Pat. No. 5,574,146
U.S. Pat. No. 5,602,244
U.S. Pat. No. 4,683,202
U.S. Pat. No. 4,682,195
U.S. Pat. No. 5,645,897
U.S. Pat. No. 4,554,101
U.S. Pat. No. 4,304,863
U.S. Pat. No. 4,237,224
U.S. Pat. No. 4,683,202
U.S. Pat. No. 5,928,906
U.S. Pat. No. 5,925,565
U.S. Pat. No. 5,935,819
U.S. Pat. No. 5,384,253
U.S. Pat. No. 5,550,318

U.S. Pat. No. 5,538,880
U.S. Pat. No. 5,610,042
U.S. Pat. No. 3,791,932
U.S. Pat. No. 4,174,384
U.S. Pat. No. 3,949,064
Ausubel et al., In: *Current Protocols in Molecular Biology*, John, Wiley and Sons, Inc, New York, 1994.
Bernard et al, *AIDS,* 12(16):2125-39, 1998.
Brett et al., *J. Immunol.,* 150:2869-2884, 1993.
Campbell, In: *Monoclonal Antibody Technology, Laboratory Techniques in Biochemistry and Molecular Biology,* Amsterdam, pp. 71-74; 75-83, 1984.
Capaldi et al., *Biochem. Biophys. Res. Comm.,* 76:425, 1977.
Carbonelli et al., *FEMS Microbiol. Lett.,* 177(1):75-82, 1999.
Celluzzi and Falo, *J. Invest. Dermatol.,* 108(5):716-20, 1997.
Ching and Inouye, *J. Mol. Biol.,* 185:501-507, 1985
Cocea, *Biotechniques,* 23(5):814-816, 1997.
Coynault et al., *Mol. Microbiol.,* 22:149-160, 1996
DeBoer et al., In *Promoter Structure and Function*, Rodriguez and Chamberlain, eds., Praeger Publishing, NY, 1982.
European Patent App. EP 266,032
Fouts et al., *Vaccine,* 13:1697-1705, 1995.
Froehler et al., *Nucleic Acids Res.,* 14(13):5399-5407, 1986.
Gefter et al., *Somatic Cell Genet.,* 3(2):231-6, 1977.
Goding, In: *Monoclonal Antibodies: Principles and Practice,* 2d ed., Academic Press, Orlando, Fla., pp. 60-66, and 71-74, 1986.
Hoiseth and Stocker, *Nature,* 291:238, 1981.
Huang et al., *J. Biol. Chem.,* 258:8139-8145, 1983.
Inouye and Inouye, *Nucleic Acids Res.,* 13: 3101-3109, 1985.
Johnson et al., In: *Biotechnology And Pharmacy*, Chapman and Hall, New York, 1993.
Klein et al., *Nature,* 327:70-73, 1987.
Kohler and Milstein, *Eur. J. Immunol.,* 6:511-519, 1976.
Kohler and Milstein, *Nature,* 256(5517):495-7, 1975.
Kornberg and Baker, DNA Replication, 2nd Ed., Freeman, San Francisco, 1992.
Kyte and Doolittle, *J. Mol. Biol.,* 157(1):105-132, 1982.
Levenson et al., *Hum Gene Ther,* 9(8):1233-6, 1998.
Maniatis, et al., Molecular Cloning, A Laboratory Manual, Cold Spring Harbor Laboratory, Cold Spring Harbor, N.Y., 1988
Miller, In: *Experiments in Molecular Genetics*, Cold Spring Harbor Laboratory, Cold Spring Harbor, N.Y., 1972
Morein et al., *Dev Biol Stand,* 92:33-9, 1998.
Nakamura and Inouye, *Cell,* 18:1109-1117, 1979.
Nociari et al., *J Immunol Methods,* 213(2):157-67, 1998.
Noriega et al., *Infect. Immun.,* 64:3055-3061, 1996.
Page et al., *Anticancer Res,* 18(4A):2313-6, 1998.
PCT Application WO 94/09699
Pelletier and Sonenberg, *Nature,* 334(6180):320-325, 1988.
Potter et al., *Proc. Natl. Acad. Sci. USA,* 81:7161-7165, 1984.
Remington's Pharmaceutical Sciences, 15$^{th}$ ed., pages 1035-1038 and 1570-1580, Mack Publishing Company, Easton, Pa., 1980.
Remington's Pharmaceutical Sciences, 18th Ed. Mack Printing Company, pp. 1289-1329, 1990.
Reznikoff and Gold, In: *Maximizing Gene Express*, Plenum Press, NY, 1986.
Roberts and Lauer, *Meth. Enzymol.,* 68:473, 1979.
Rosenberg et al., *Science,* 223:218-1321, 1986.
Sambrook et al., In: *Molecular Cloning: A Laboratory Manual*, 2nd Ed., Cold Spring Harbor Press, Cold Spring Harbor, N.Y., 1989.
Schmeiger, *Mol. Gen. Genetics,* 119-175, 1972.
Shine and Dalgarno, *Nature,* 254:34-38, 1975.
Simpson et al., *Gastroenterology,* 115(4):849-55, 1998.
Sizemore et al., *Science,* 270:299-302, 1995
Steinman et al., *Hum. Immunol.,* 60(7):562-567, 1999
Stocker et al., *Develop. Biol. Standard,* 53:47, 1982.
Tur-Kaspa et al., *Mol. Cell Biol.,* 6:716-718, 1986.
Von Heijne, *J. Mol. Biol.,* 184(1):99-105, 1985.
Yamagata et al., *J. Biol. Chem.,* 256:2194-2198, 1981.
Yang et al., *Proc. Natl. Acad. Sci. USA,* 87:9568-9572, 1990.

What is claimed is:

1. An isolated, attenuated *Salmonella typhimurium* bacterium lacking a functional lipoprotein encoded by an endogenous lpp gene and comprising a recombinant expression cassette.

2. The bacterium of claim 1, wherein the bacterium lacks the lpp gene.

3. The bacterium of claim 1, wherein the lpp gene of the bacterium is mutated.

4. The bacterium of claim 3, wherein the lpp gene of the bacterium is incapable of surface expression of the functional lipoprotein.

5. The bacterium of claim 4, wherein the lpp gene has a deletion, substitution, or insertion mutation.

6. The bacterium of claim 5, wherein the lpp gene has a deletion.

7. The bacterium of claim 3, wherein the lpp gene expresses a non-functional truncated lipoprotein.

8. The bacterium of claim 5, wherein the deletion, the substitution, or the insertion mutation is a point mutation.

9. The bacterium of claim 5, wherein the deletion, the substitution, or the insertion mutation introduces a stop codon in the lpp gene.

10. The bacterium of claim 1, wherein the bacterium is comprised in a pharmaceutically acceptable composition.

11. The bacterium of claim 10, wherein the pharmaceutically acceptable composition further comprises an adjuvant.

12. A pharmaceutical composition comprising:
   (a) an isolated, attenuated *Salmonella typhimurium* bacterium lacking a functional lipoprotein encoded by an endogenous lpp gene; and
   (b) a pharmaceutically acceptable carrier.

13. The pharmaceutical composition of claim 12 further comprising an adjuvant.

14. The pharmaceutical composition of claim 12, wherein the lpp gene of the bacterium is mutated.

15. The pharmaceutical composition of claim 14, wherein the lpp gene of the bacterium is incapable of surface expression of the functional lipoprotein.

16. The pharmaceutical composition of claim 14, wherein the lpp gene has a deletion, substitution, or insertion mutation.

17. The pharmaceutical composition of claim 16, wherein the lpp gene has a deletion.

18. The pharmaceutical composition of claim 17, wherein the lpp gene expresses a non-functional truncated lipoprotein.

19. The pharmaceutical composition of claim 16, wherein the deletion, the substitution, or the insertion mutation is a point mutation.

20. The pharmaceutical composition of claim 16, wherein the deletion, the substitution, or the insertion mutation introduces a stop codon in the lpp gene.

21. The bacterium of claim 1, wherein the expression cassette encodes an antigen.

22. The bacterium of claim 21, wherein the antigen is a fusion protein.

23. The bacterium of claim 22, wherein the fusion protein is expressed on the bacterium surface.

24. The bacterium of claim 21, wherein the antigen is from a pathogenic organism.

25. The bacterium of claim 24, wherein the pathogenic organism is a bacterium, a fungus, a virus, a nematode, a trypanosome, or an amoeba.

26. A method for producing a pharmaceutical composition comprising:
   (a) obtaining an isolated, attenuated *Salmonella typhimurium* bacterium lacking an endogenous lpp gene encoding a functional lipoprotein; and
   (b) formulating the bacterium into the pharmaceutical composition comprising the bacterium.

* * * * *

UNITED STATES PATENT AND TRADEMARK OFFICE
CERTIFICATE OF CORRECTION

| | | |
|---|---|---|
| PATENT NO. | : 7,655,241 B2 | Page 1 of 1 |
| APPLICATION NO. | : 10/394517 | |
| DATED | : February 2, 2010 | |
| INVENTOR(S) | : Klimpel et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 379 days.

Signed and Sealed this

Twenty-third Day of November, 2010

David J. Kappos
*Director of the United States Patent and Trademark Office*

SEQUENCE LISTING

```
<160> NUMBER OF SEQ ID NOS: 12

<210> SEQ ID NO 1
<211> LENGTH: 240
<212> TYPE: DNA
<213> ORGANISM: Salmonella typhimurium
<220> FEATURE:
<221> NAME/KEY: CDS
<222> LOCATION: (1)..(240)

<400> SEQUENCE: 1 atg aac cgt act aac cag ctg atc tta ggt gca gta gtt ctg ggt tcc      48
Met Asn Arg Thr Asn Gln Leu Ile Leu Gly Ala Val Val Leu Gly Ser
  1               5                  10                  15 acg tta ctg gca ggt tgt tca agc aac gct aaa atc gat cag gtt tct      96
Thr Leu Leu Ala Gly Cys Ser Ser Asn Ala Lys Ile Asp Gln Val Ser
             20                  25                  30 tcc gat gta cag acg ctg agc gct aaa gtt gag caa ctg agt aat gac     144
Ser Asp Val Gln Thr Leu Ser Ala Lys Val Glu Gln Leu Ser Asn Asp
         35                  40                  45 gta aat gca atg tgc tcc gac gtt cag gct gct aaa gac gat gct gct     192
Val Asn Ala Met Cys Ser Asp Val Gln Ala Ala Lys Asp Asp Ala Ala
     50                  55                  60
```

```
cgc gcg aac caa cgt ctg gac aac aaa gta ttc cgc atc tgt aaa taa    240
Arg Ala Asn Gln Arg Leu Asp Asn Lys Val Phe Arg Ile Cys Lys
 65                  70                  75                  80

<210> SEQ ID NO 2
<211> LENGTH: 79
<212> TYPE: PRT
<213> ORGANISM: Salmonella typhimurium

<400> SEQUENCE: 2

Met Asn Arg Thr Asn Gln Leu Ile Leu Gly Ala Val Val Leu Gly Ser
 1               5                  10                  15

Thr Leu Leu Ala Gly Cys Ser Ser Asn Ala Lys Ile Asp Gln Val Ser
                20                  25                  30

Ser Asp Val Gln Thr Leu Ser Ala Lys Val Glu Gln Leu Ser Asn Asp
            35                  40                  45

Val Asn Ala Met Cys Ser Asp Val Gln Ala Ala Lys Asp Asp Ala Ala
         50                  55                  60

Arg Ala Asn Gln Arg Leu Asp Asn Lys Val Phe Arg Ile Cys Lys
 65                  70                  75

<210> SEQ ID NO 3
<211> LENGTH: 237
<212> TYPE: DNA
<213> ORGANISM: Salmonella typhimurium
<220> FEATURE:
<221> NAME/KEY: CDS
<222> LOCATION: (1)..(237)

<400> SEQUENCE: 3 atg aag cgt act aaa ctg gta ctg ggc gcg gta atc ctg ggt tct act    48
Met Lys Arg Thr Lys Leu Val Leu Gly Ala Val Ile Leu Gly Ser Thr
 1               5                  10                  15 ctg ctg gct ggt tgc tcc agc aac gct aaa atc gat cag ctg tct tct    96
Leu Leu Ala Gly Cys Ser Ser Asn Ala Lys Ile Asp Gln Leu Ser Ser
                20                  25                  30 gac ctt cag act ctg aac gct aaa gtt gac cag ctg agc aac gac gtg   144
Asp Leu Gln Thr Leu Asn Ala Lys Val Asp Gln Leu Ser Asn Asp Val
            35                  40                  45 aac gca atg cgt tgc gac gtt cag gct gct aaa gac gac gca gct cgc   192
Asn Ala Met Arg Cys Asp Val Gln Ala Ala Lys Asp Asp Ala Ala Arg
         50                  55                  60 gct aac cag cgt ctg gac aac cag gct act aaa tac cgt aag taa       237
Ala Asn Gln Arg Leu Asp Asn Gln Ala Thr Lys Tyr Arg Lys
 65                  70                  75

<210> SEQ ID NO 4
<211> LENGTH: 78
<212> TYPE: PRT
<213> ORGANISM: Salmonella typhimurium

<400> SEQUENCE: 4

Met Lys Arg Thr Lys Leu Val Leu Gly Ala Val Ile Leu Gly Ser Thr
 1               5                  10                  15

Leu Leu Ala Gly Cys Ser Ser Asn Ala Lys Ile Asp Gln Leu Ser Ser
                20                  25                  30

Asp Leu Gln Thr Leu Asn Ala Lys Val Asp Gln Leu Ser Asn Asp Val
            35                  40                  45

Asn Ala Met Arg Cys Asp Val Gln Ala Ala Lys Asp Asp Ala Ala Arg
         50                  55                  60
```

```
        Ala Asn Gln Arg Leu Asp Asn Gln Ala Thr Lys Tyr Arg Lys
         65                  70                  75

<210> SEQ ID NO 5
<211> LENGTH: 11684
<212> TYPE: DNA
<213> ORGANISM: Escherichia coli
<220> FEATURE:
<221> NAME/KEY: CDS
<222> LOCATION: (293)..(529)

<400> SEQUENCE: 5
atttgtatat cgaagcgccc tgatgggcgc ttttttttatt taatcgataa ccagaagcaa      60
taaaaaatca aatcggattt cactatataa tctcacttta tctaagatga atccgatgga     120
agcatcctgt tttctctcaa ttttttttatc taaaacccag cgttcgatgc ttctttgagc     180
gaacgatcaa aaataagtgc cttcccatca aaaaatatt ctcaacataa aaactttgt      240 gtaatacttg taacgctaca tggagattaa ctcaatctag agggtattaa ta atg aaa     298
                                                         Met Lys
                                                           1 gct act aaa ctg gta ctg ggc gcg gta atc ctg ggt tct act ctg ctg      346
Ala Thr Lys Leu Val Leu Gly Ala Val Ile Leu Gly Ser Thr Leu Leu
         5                   10                  15 gca ggt tgc tcc agc aac gct aaa atc gat cag ctg tct tct gac gtt      394
Ala Gly Cys Ser Ser Asn Ala Lys Ile Asp Gln Leu Ser Ser Asp Val
 20                  25                  30 cag act ctg aac gct aaa gtt gac cag ctg agc aac gac gtg aac gca      442
Gln Thr Leu Asn Ala Lys Val Asp Gln Leu Ser Asn Asp Val Asn Ala
         35                  40                  45                  50 atg cgt tcc gac gtt cag gct gct aaa gat gac gca gct cgt gct aac      490
Met Arg Ser Asp Val Gln Ala Ala Lys Asp Asp Ala Ala Arg Ala Asn
                 55                  60                  65 cag cgt ctg gac aac atg gct act aaa tac cgc aag taa tagtacctgt       539
Gln Arg Leu Asp Asn Met Ala Thr Lys Tyr Arg Lys
                 70                  75 gaagtgaaaa atggcgcaca ttgtgcgcca ttttttttgt ctgccgttta ccgctactgc     599
gtcacgcgta acatattccc ttgctctggt tcaccattcc gcgctgactc tactgaaggc     659
gcattgctgg ctgcgggagt tgctccactg ctcaccgaaa ccggatacce tgcccgacga     719 tacaacgctt tatcgactaa cttctgatct acagcctttat tgtctttaaa ttgcgtaaag     779
cctgctggca gtgtgtatgg cattgtctga acgttctgct gttcttctgc cgatagtggt     839
cgatgtactt caacataacg catcccgtta ggctccacgg aatatttcac cggttcgttg     899
atcactttca ccggcgttcc cgtccgcacg ctggagaaca aggctttaat atccggtgca     959
ttcatgcgaa tacaccctga actgacgcgc aaaccgacgc tgtccggcgc actggtacca    1019
tgaatgaggt attcgccatt accatgcgcg aggcgcagtg cgtaacgtcc tagcgggtta    1079
tttggtccgg caggaacgac tggcggtaat ttaatgccac gctccagcga acgctgacga    1139
atgcctgccg taggcgtcca ggttgggtta gggattttct gcccaacacg cgtttccatc    1199
accggcgttt ccagccctg caatccaata cctattggat aaacctgcac aatattttct    1259
cccggcggat aataataaag cgcagctct gcaaggttaa cgataatccc ctgacgcggt    1319
gcatcaggta ataacagttg tgaaggaata gttatcgtcg taccaggttt tggcaccggg    1379
gcgatagtgt tattggcttc aaggatcaac attgccgcag tatcaaaacg tcgggcaata    1439
gcctgaaggt tttatcccc ttcttgcacc gtatacgttt gatttttgccc aaccagtcgg    1499 cttccggttg gtggtagcgg ataatcaacc gcccaggcag cctggatggc gctaaaagcg    1559
```

```
ccgataagcg tgagtgtaag caaagacgcg cgtttcattg taaacctcct gtatttgccg    1619
gagactcacg ctgaaacgtc ggatggcgct tatgttcacc tgaaaccaaa acactcctgt    1679
gcaggtcagt gtaaacattg accatccggc aatgtgagcc aaccggatga aagctgtcct    1739
tttagtttag ctaagtgcag cggctttggc gcgaattgcg cgaatcatcg cttccagacc    1799
ttgtgaacga gatggggtga gatgttgggt gagcgccatt ttttcaaacc acggacgcac    1859
atcgaaattg acaatatcct gcggcgtcat ctgatcgtag agaataaaga cgaccgcaat    1919
aagccctttc acaatcgccg catcgctgtc gccctgtaat tcaataattc ctgggcatt     1979 ctggcgcatg acaatccaca cctgactctg acagccctga atgctatttt gtggacttct    2039
gtcttcgtcg cgtaattctg gcagacgctg gcccagctca ataatgtaga gatatttctc    2099
ttcccagttg gcgcagcgta aaaaattacg cagcaacttt tctttatccg gcaataaagc    2159
catagtgcct ccctgttatc ccagcaaacg gtgaatacgt tgcaggccgg tcaccagacg    2219
atccacttct tcatgggtgt tatacatggc cagcgacgcc cgacacatcg cagggacgtt    2279
gtaataggcc atcaatggca ttgcgcagtg atgtccggta cgcacagcaa tgccgtaatt    2339
atcgagaaaa ctgccaacat cataggcgtg gtgtttaccg agattaaaag caataacgcc    2399
aagcctgttt tgtgggccat agagagtgag atccggtaca gattccagct gtgatagcgc    2459
ataatgcatc agattctgtt catactcggc tatgttatta agcccagcg ccgaaacata     2519 ctccagcgcc gcgccaagac caatgatgcc cccggtattg ggtgtaccgg cttcaaaccg    2579
ccatggtgct ttggtccagg tagtgccttc actcaggctg acggtggcga tcatagaacc    2639 gccccttcc cacggcggca tctcctgcaa caaggcttct ttcacataaa gaatgccaat     2699
tccggtgggg ccatacagtt tatgcccgga gaacacgtaa aagtcgcaat ccagcgcctg    2759
aacatccacc ggatgatgca tcaccgcctg agcgccatcc accagcactt ttgcgccatg    2819
ctggtgcgca agcgtgatca tttccgccag tggattttct gtgccaagca cgttggagac    2879
atgagtaatt gccagcaggc gagttttctc atcaaacagc gtaggcagcg tctccagttg    2939
caacgtacca tcgggattga gcgggatcac acgcagctct cgccaacgc gtgcgcaaag     2999 catctgccag ggaacaatgt tagcgtggtg ctccatctga ctgatgatga tgttatcgcc    3059
cgcccgcacg ttgctgttgc cccagctatt ggcgaccaga ttgatcccct ccgtcgtgcc    3119
gcggacgaac accagctctt ccgccgaacg ggcattaata acagcgatg cccgcttgcg     3179 cacgttctcc attttctcgg tcgcctgggc gcttaaggta tgaataccac gatgcaccgc    3239
cgcgtagcca tgacgataaa actcggcctc ggcgtcaatc acctggctcg gtttctgcgc    3299
actggcggcg ctgtcgagat aagccagcgg caaaccgttt acctcacgcg aaagcaccgg    3359
aaagtcggcc cgcactttgt cgacggaaaa atcatcttg cacctcctgg cagccgttga     3419
ccgattcggg ccagcacctg ctgtttaagc ccctcatcac gcagtgcttc cgtcagttcg    3479
gcagcgaagg cgtaaatgat catctgctgg gcatcctgct gattgatccc gcgcgagcgc    3539
agatagaata tctgttcatc atcaatacgc cccaccgtcg cgccgtggct gcatttcaca    3599
tcatctgcat agatttccag ctgcggtttc gtatccactt ccgccagttt gcccatcagc    3659
agattgttgt tggtcatctg accatccgtt ttgatggcgt gctgcgcgac gttgatcaaa    3719
ccgttaaata ccgcgcggcc tttgtcgctg acgatagttt tgtgcaactg tcggctgtta    3779
caaaaacctt tattgtgttc cagccaggta cgggtatcac acacctcgtt tttcaccggc    3839
atcgccaggc tattgatccg cagcgtgctg ttttcgccat tgagttgcgt actggtgttg    3899
```

```
tgtcgtaaca ctgcgccacc cagcaggaaa ctgtggctaa atgcggtggc atcctcagcc   3959
agcaacaaat cgttatgagc aaagtggtga ctgagcgggt tttcaaacgc cagcttgata   4019
tgctgcaagt gggcattcgc tgcgacgttg atagtgaacc gtgccccggt aaaatgacga   4079
gcatcattca ggctgacaaa atgttcgatc accgttgctt cggcaccttc cgccagatcc   4139
agatgatgtc ggtaatgggc agtgttcacc tcttcacctg ccacgccctg ggtgatatgc   4199
attaacagca atggctttgc cggccgttga ccgcgcttca cggcgatatg cgtcacgctt   4259
tgtgccaggc tttccgtcaa atgcagaaac acttccgcct gaatagcgtc gggtaaaccc   4319
tgacggtcgt cgttaatgct cacttcatat ccgctgcctt cagttgcatc gctcagtgcg   4379
ggcacgtaac gcccatcgac aaacaccagc cgcacggagt ctaacgttaa cgctaaggca   4439
tcacgctgct gtgggatat ctctcccgca atgctgacaa actggctatt gatcagccct   4499
tccagcggcg tatatttcca gttttcatgt ttacgtgtcg gcagtccggt acgcagcaat   4559
tgttgtaaat gctgctgtgc ttgcggggag cgttttgtcc cttcagcttc aaacaagtga   4619
tgccactgtt gcagcgcgtt actgctgttc ggtaagccag ccataaccct gctcctccag   4679
ttgtttgacc aacgtgaaat cgccggattt cacaattcgt ccctgatata gcacatgaac   4739
gtaatcaggc ttgatgtagt cgagaatgcg ttggtagtgc gtaacaatga tgaatgagcg   4799
cttgccatca cgcagcgagt tcacgccatc ggcgaccact tttaatgcgt caatatccag   4859
cccggagtcc gactcatcaa gaatgcataa ctccggttcc agcaccgcca tttgcaaaat   4919
atcgttgcgc tttttctcgc cgccggaaaa accaacgttt accgaacggg ttaataaatc   4979
ttccggcatc ttcaggagag cgattttctc ttccatcaaa tcctgaaaat caaagcggtc   5039
gagcgttcc tggccgcgat agctgcgcac cgcattaagt gccgtttgca ggaaaaactg   5099
gttactgaca cctggaatct ccaccggata ctggaaggcc ataaagatgc cttcgcccgc   5159
gcgatcttcc ggcgacagcg caagcaaatc tttgcctttg aactcaaccg tgccgcccgt   5219
cacttcataa tcttctcgcc cggcaagcgt tgccgataag gtacttttgc ccgaaccgtt   5279
tggcccata atggcgtgaa cttcgccggg atgaacgtcg aggcttaatc cgcgcaggat   5339
agctttatct tccacgctga cgtgtaaatc tttaatactt aacatgttta ttccttatcc   5399
gacgctgtgt tcaagactga tggcgaggag tttttgtgct tcaacggcaa attccaacgg   5459
cagctccgag aacacgtctt tgcagaaacc gttaacaatc atcgagatgg cgtcttcttc   5519
gctgatcccg cgttgcaggc agtaaaacag ttgatcttca ccaatacgtg atgtcgttgc   5579
ctcgtgttcc agttgcgcac tattgttacg acactcaaca tacgggaagg tatgcgcccc   5639
acaattagcg ccaatcagca ttgagtcgca ctgagtgaaa ttgcgcgcat tggttgccgt   5699
cggcatgatt ttcactaagc cgcgataact gttctgacta tgtccggcag agatcccttt   5759
cgagataatg gtcgatttgg tgttttttacc gatgtggatc atcttggtgc cggtatccgc   5819
ttgctgatga ccgctggtca gcgccactga gtaaaactca ccaatggagt tatcgccgcg   5879
caaaatgcag ctgggatatt tccacgtaat cgctgacccg gtttctgatt gcgtccatga   5939
cattttgctg ttttcgcctt cgcacaaagc acgcttggtg acgaagttga gaataccgcc   5999
ggtgttgtta tcgccaggaa accagttttg taccgtggaa tatttcacct cggcgttttt   6059
atggatgatg acttccacca ctgccgcgtg taactgatag ctgtcacgca ccggagcgga   6119
acagccttca atgtagctga cgtagctgtc ttcgtcggcc accagaatgg tgcgctcaaa   6179
ctgcccggtt ttttctgcgt taatgcgaaa ataggtggaa agttccatcg ggcagcgcac   6239
gccttttaggc acataaataa acgtaccatc agaggctacc gccgcattaa gcgcggcaaa   6299
```

```
gaagttgtca ttccccggca ccacggtgcc gagatattta cgcaccagtt ccgggtgatc    6359
gtggatcgcc tcaccaaagg aacagaaaat aattccctgc tccgccagtt tttcgcgata    6419
agtagtggca accgaaactg agtcgaaaat ggcatccacc gccacctctt tgccttcccg    6479
cacgggaacg cccaactgct caaacgccgc ctccacctct ttacttaaaa aggcgttcgc    6539
gccagtttgc tgcaccgcgc caggttcaga cgcgcaagtg tcgtcacaat taccgcacga    6599
tggtgctgag tagtagctgt aatcctgata attcagcttg tcgtagtgcg ctttcaacca    6659
gtgcggttct tccatctcca gccatgcgcg ataggcgttt agacgaaact ccagcatcca    6719
ctccggctca ttacgcttcg ccgaaattgc gcgcaccacc tcttcgttta tccccttttgc   6779 cagctcatcg gtggctaact gggtgaagaa tccttcttta taattcagcg ggccgccggt    6839
ccaggttttg acatcgtcag ttgcttcagt attacgagac atagtaccgc ctatacccca    6899
aagctttcgc cacagccaca ttcattctgg gctttagggt tgtgaaattt gaatatctga    6959
ttaagtcctt cacgaacgaa atcgacttcc gtgccatcaa taaacggcat cgcttgcagc    7019
gggacaaaca gcttcgcgcc gtcgtgttca aacagcagat cgtctttgtc cggctcgcta    7079
acactgtcga gcacatagcc aaagcccgcg cagcccgttt gcttcacgcc taagcgcacg    7139
ccgaccatac ccggctgctt tgccaccagc tcacggatgt gtatcgccgc tgcgggtgtc    7199
agcgttaagc cttgccaggc gaaatcttgt gggttaaagg ttcctgaatg catgtccatc    7259
gatttacctc acttcatcgc tttcagcgta taacagcatg ttagtgataa tgattatcag    7319
ttcaacccag caaacgcagg ggcttaccg taaaacatgc ttttttgcctg cttttaataa    7379 gcatagaccc tgatgtgtgg gttaacaggc acgctaagaa ttaggtatct cattgttaga    7439
taatggttat tatctaagga gcattaaggc tgtgatgaaa agaaaaagt tgtattgaaa     7499 atgactattt aagagatagg taaaaaagtg cagcgttcag aaataagaaa acccttaagt    7559
ctgtgcgaca caggcttaag ggtttctacc ccatccggcg cttatctccg gcactctcag    7619
tggcttagct cttgaagggg cgataagaat aatctcataa agctaacccg ccgttttaac    7679
acaaactgcg attagtatta ttttttgaaca atatcaggcg gtagataagc agtattaaga    7739
aggtcatcga acctggacgg aggttaatcc aggtcgattt ggcgaacttg cggcattaag    7799
tcaggatcaa tgcacgccca gacgccaggc aaagtagatt tcttctttta attcagcaga    7859
agagagagta agcaggtcag caaattcaag ttctagttgt ttcagacgtt tgagatattg    7919
ggcaggtgaa agattgctct ggtcacggcg taaaaattca atggccagct gggtgggatc    7979
aagttgagta gacatagcat cctcgctttt agacaagacc tgcacagtat accaccgttt    8039
actgtgcaga taatgaccaa aagcaatatg cgtcacactt ttctggtgac aacgtcacaa    8099
aatggcggtc gtcaatcgtg acgaacagca caaacgccct ttctcatcga agattcaat    8159 ctgccagacc tggtgacgcg aaccgagatg caacggtttg catacgccgc gcacccgccc    8219
ttctcgtgcc gagcggacgt ggttagcatt gatttccaga ccaaccactt tttgctcacc    8279
ttcggtacat aaataaccgg caacggaacc gatactttcg gccagtacca cggatgctcc    8339
tccatgcagc aacccgaaag gctgctttgt ccgcgagtct actggcattg tcgcttcaag    8399
ggtgtcatca ccaatatgtt caaagcgaat atccaggaac cccaccatgt ttccttcacc    8459
catagcattc agtgcttcca gggtgatttt ccgtttccat atcatttaat aatctccagt    8519
aaagcctgca caggatggcg tacccccgtg ccttcaaccc gttttacctg gctacgcag    8579 gaatatccgg tcgccagaca gcggttacgc ggcagtcgct gcatagcctg atgccaggat    8639
```

```
aactcatagc tcccgagcga attttcatgg tttttcgctt catgtccgta agtccctgcc    8699
atgccgcagc aacccacgct gacatttccc agtttcgcgc caaaacgggc aaatatcgcg    8759
gcccattgtg ctggcgcacc cggcaaggcg gtaacttcgg tacagtgacc aaagaaatac    8819
catgattcac cgctgactgt agccactggc tgtgactcaa gtgcgcttgc cagccattca    8879
ttcgccagta agacgttaaa ctcgccacgc tcctcgccca gcgccagttt atattcatcg    8939
cgataacaaa gtaccagcgc cggatcgacg cccaccattg gcatacccag cttcgccata    8999
cggttgagga aatccgccgt cttttcgcc gtcttcgcaa aacgattaag aaaacccttta    9059 atatgctggg ctttgccatt tggcgaaaat ggcagtaaca caggctggaa acctaatttt    9119
tcgaccagac ggacaaaatc cgccaccact tgcgcatcgt aatagctggt aaaggggtcc    9179
tgcaccacca acactgtgcg cgctttctgc tctgcattga gagattcaag ctgttccagc    9239
gtcatgtttg ccgagcgatg ccccaccatt tgttgttgta gcgagggggac cgacagcagc    9299 ggcaaatcaa ccatgccgat atgttttttcc gagagtttgc gcaccagcgg ctggttaatg    9359
aagaagttaa aggttttcgg cgcgcgtgcc atcagcggcg cgtagctctc gaccgtagcg    9419
acgaggtggt cgcgcagcgg gcgtaaataa cgggtgtgat agagctgcag aaaacgagag    9479
cgaaactccg gcacatcaat tttgatgggg cactgggtcg aacacgcttt acaggccaga    9539
cagcccgaca tcgcctcttt gacttcgtgt gagaagtcat attcgccttt attcgcatgc    9599
cagctattgc gcgtgcgggc aattaacgtc cgcaaactga cgccggattc aggcagttct    9659
tgttccagtt tgagtggatc aacgccgcga tccgccaaca aacgcagcca ttcacgcacc    9719
agcgttgcgc gcccttttcgg tgaatgaatc cggttctggg tgatcttcat cgacggacac    9779
atcggactac gggcatcaaa gttgaagcat aaaccgttgc cgttacactc catcgcaccg    9839
cgccactgct ggcgtaccgc aatggggatc tgccgatcga atgtaccgcg cttcaccgcg    9899
tccactttca tcatcggcgc atcgagacct tctggcgggc aaatcttccc tgggttgagt    9959
cggttatgcg ggtcaaatgc cgctttcact ttgcgcagtt ctgcaaaaag ttcctcaccg   10019
aaaaacgccg ggctgtattc agcgcgaaaa cctttgccgt gctcgcccca caacaaacca   10079
ccgtatttcg cagtcagcgc caccacgtca tcagagattt gcttcatcaa aatctcttgt   10139
tgaggatcgc acatatccag cgctggacgg acgtgcaaga cacctgcgtc gacgtgaccg   10199
aacataccgt agcttaagcc gtggctgtcg agcagcgcgc gaaattcagc aatataatcc   10259
gccaggtgtt ccggcggtac gcaggtatcc tcagcaaacg gaattggctt agcggcacct   10319
ttggcattgc caagcagacc aacggctttt ttgcgcattg catagatacg ttcaaccccc   10379
gccagctcac ggcacacctg ccagccgatg acacctgctt gatgactggc gatcagctca   10439
tccaaccgcg cacagagtgc atttacccgc tcatcaatca gcgcctcatc atcaccagca   10499
aattccacaa tgttcagccc gagcatctct tggtcaggca catcggtaat caactcgctg   10559
acggaatgcc agacaatatc ttcccgcgcc agattcagca cttttgagtc caccgtctct   10619
accgaaagcg cccgcgcctc aaccataaac ggcgcgttac gcagcgcaga gtcaaaagag   10679
tcatatttga cgttcaccag acggcgcact ttaggcaagc gtgtaatatc cagccgcgct   10739
tcggtaataa aggccagcgt cccttctgaa cccgtcagaa tgcgcgtcag gtcgaactcg   10799
gtcatctcat cgttaaagac atgacgcaga tcgtaaccgg taagaaagcg gttaagtttg   10859
gggaagttgt cgataattaa ctggcgttgc tgacggcaac gttgataaac cgtgttataa   10919
attcgcccga ttgtggtatt ggatttaccc agcgtttccg ccaattcgac gggtaaaggt   10979
tgcgtatcga gaatatcgcc ccccaacaac accgcgcgta cgccaagtac gtgatctgac   11039
```

```
gttttgccat agaccagcga tccctgaccg gatgcatcgg tattgatcat cccaccgagc    11099
gttgcccggt tgctggtcga aagttccggc gcaaaaaagt agccgaacgg tttcaggtac    11159
tgattgagtt gatcttttat caccccggcc tcaacgcgca cccagccctc ttcagggtta    11219
atttcgatga tgcggttcat atggcgggac atatcaacaa taatcccctg gttgagcgcc    11279
tgaccgttag tgccggtgcc gccgccgcgg ggggtaaaga tcagcgatga atagcgttcc    11339
tgcgcggcaa gacgggcgat cagcgccaca tctgcggttg aacgcggaaa taccaccgca    11399
tcggggagaa gttggtaaat actgttgtcg gtcgacattg tcagacgatc ggcataactt    11459
gtcgccgtat cgccggtaaa accttgttgc tccagctctt gcaaaaaatt aagcaccagt    11519
tgaacgacgc cgggtgcctg ggaaatctgt ggaatcatta tattgaccct ttcctgcggt    11579
ctgtgatgta ggtcgataca ctattctttc aggctgctgc aatagcgcac tgaaaggtga    11639
tgtttgttta ctctatggat ttcgtgttgc aggaaggcgg caagc                   11684
```

<210> SEQ ID NO 6
<211> LENGTH: 78
<212> TYPE: PRT
<213> ORGANISM: Escherichia coli

<400> SEQUENCE: 6

```
Met Lys Ala Thr Lys Leu Val Leu Gly Ala Val Ile Leu Gly Ser Thr
  1               5                  10                  15

Leu Leu Ala Gly Cys Ser Ser Asn Ala Lys Ile Asp Gln Leu Ser Ser
              20                  25                  30

Asp Val Gln Thr Leu Asn Ala Lys Val Asp Gln Leu Ser Asn Asp Val
          35                  40                  45

Asn Ala Met Arg Ser Asp Val Gln Ala Ala Lys Asp Asp Ala Ala Arg
      50                  55                  60

Ala Asn Gln Arg Leu Asp Asn Met Ala Thr Lys Tyr Arg Lys
  65                  70                  75
```

<210> SEQ ID NO 7
<211> LENGTH: 78
<212> TYPE: PRT
<213> ORGANISM: Salmonella typhimurium

<400> SEQUENCE: 7

```
Met Asn Arg Thr Lys Leu Val Leu Gly Ala Val Ile Leu Gly Ser Thr
  1               5                  10                  15

Leu Leu Ala Gly Cys Ser Ser Asn Ala Lys Ile Asp Gln Leu Ser Ser
              20                  25                  30

Asp Val Gln Thr Leu Asn Ala Lys Val Asp Gln Leu Ser Asn Asp Val
          35                  40                  45

Asn Ala Met Arg Ser Asp Val Gln Ala Ala Lys Asp Asp Ala Ala Arg
      50                  55                  60

Ala Asn Gln Arg Leu Asp Asn Gln Ala Thr Lys Tyr Arg Lys
  65                  70                  75
```

<210> SEQ ID NO 8
<211> LENGTH: 79
<212> TYPE: PRT
<213> ORGANISM: Salmonella typhimurium

<400> SEQUENCE: 8

```
Met Asn Arg Thr Asn Gln Leu Ile Leu Gly Ala Val Val Leu Gly Ser
  1               5                  10                  15
```

```
Thr Leu Leu Ala Gly Cys Ser Ser Asn Ala Lys Ile Asp Gln Leu Ser
            20                  25                  30

Ser Val Asp Gln Thr Leu Ser Ala Lys Val Glu Gln Leu Ser Asn Asp
        35                  40                  45

Val Asn Ala Met Arg Ser Asp Val Gln Ala Ala Lys Asp Asp Ala Ala
    50                  55                  60

Arg Ala Asn Gln Arg Leu Asp Asn Lys Val Phe Arg Ile Cys Lys
 65                  70                  75

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 9
gtggatccta tgcagaacac ggtcagcg                                         28

<210> SEQ ID NO 10
<211> LENGTH: 29
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 10
agctcgagct agattgagtt aatcttcca                                        29

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 11
atctcgagta ctgcgaaggc tactgcgtcc                                       30

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 12
aagggccctt cgctggcgat gtataac                                          27
```